(12) United States Patent
Fujimagari et al.

(10) Patent No.: US 8,128,580 B2
(45) Date of Patent: Mar. 6, 2012

(54) GUIDE WIRE

(75) Inventors: Hideki Fujimagari, Irvine, CA (US); Hiroshi Yagi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 933 days.

(21) Appl. No.: 12/057,763

(22) Filed: Mar. 28, 2008

(65) Prior Publication Data

US 2009/0157050 A1  Jun. 18, 2009

Related U.S. Application Data

(60) Provisional application No. 60/907,399, filed on Mar. 30, 2007.

(30) Foreign Application Priority Data

Mar. 29, 2007  (JP) ................................. 2007-089889

(51) Int. Cl.
*A61B 5/00* (2006.01)
*A61M 25/00* (2006.01)

(52) U.S. Cl. ...................................... 600/585

(58) Field of Classification Search ............ 600/585
See application file for complete search history.

(56) References Cited

U.S. PATENT DOCUMENTS

| | | |
|---|---|---|
| 4,884,579 A | 12/1989 | Engelson |
| 4,925,445 A | 5/1990 | Sakamoto et al. |
| 5,069,226 A | 12/1991 | Yamauchi et al. |
| 5,095,915 A | 3/1992 | Engelson |
| 5,238,004 A | 8/1993 | Sahatjian et al. |
| 5,269,759 A | 12/1993 | Hernandez et al. |
| 5,368,049 A | 11/1994 | Raman et al. |
| 5,402,799 A | 4/1995 | Colon et al. |
| 5,411,476 A | 5/1995 | Abrams et al. |
| 5,452,726 A | 9/1995 | Burmeister et al. |
| 5,497,785 A | 3/1996 | Viera |
| 5,497,786 A | 3/1996 | Urick |
| 5,498,250 A | 3/1996 | Prather |
| 5,772,609 A | 6/1998 | Nguyen et al. |
| 5,797,857 A | 8/1998 | Obitsu |
| 5,876,356 A | 3/1999 | Viera et al. |
| 5,924,998 A | 7/1999 | Cornelius et al. |
| 5,951,494 A | 9/1999 | Wang et al. |
| 6,001,068 A | 12/1999 | Uchino et al. |
| RE36,628 E | 3/2000 | Sagae et al. |
| 6,093,157 A | 7/2000 | Chandrasekaran |
| 6,165,292 A | 12/2000 | Abrams et al. |
| 6,234,981 B1 | 5/2001 | Howland |
| 6,390,992 B1 | 5/2002 | Morris et al. |
| 6,520,923 B1 | 2/2003 | Jalisi |
| 6,679,853 B1 | 1/2004 | Jalisi |
| 2004/0030266 A1 | 2/2004 | Murayama et al. |
| 2004/0039308 A1 | 2/2004 | Murayama et al. |
| 2004/0039309 A1 | 2/2004 | Murayama et al. |
| 2005/0152731 A1 | 7/2005 | Mishima et al. |
| 2006/0189896 A1* | 8/2006 | Davis et al. .................. 600/585 |

* cited by examiner

*Primary Examiner* — Brian Szmal
(74) *Attorney, Agent, or Firm* — Buchanan Ingersoll & Rooney PC

(57) ABSTRACT

A guide wire includes a wire body having an elongate reshapeable section at its distal part. The guide wire may include a surface of the reshapeable section being provided with a plurality of grooves extending in a direction different from the longitudinal direction of the reshapeable section.

5 Claims, 14 Drawing Sheets

GUIDE WIRE

This application claims priority under 35 U.S.C. §119(e) to U.S. Provisional Application No. 60/907,399 filed on Mar. 30, 2007, the entire content of which is incorporated herein by reference. This application is also based on and claims priority to Japanese Application No. 2007-89889 filed on Mar. 29, 2007, the entire content of which is incorporated herein.

TECHNICAL FIELD

The present invention generally relates to an elongated medical device. More specifically, the invention pertains to a guide wire.

BACKGROUND DISCUSSION

Guide wires are used to insert and guide a catheter to a target site to treat cites at which open surgery is difficult or which require low invasiveness to the body or in examination or treatment of a cardiac disease through cardioangiography or the like.

For example, in the process of PCI (Percutaneous Coronary Intervention), a treatment is conducted as follows. The distal end (tip) of a guide wire while protruding from the distal end of a balloon catheter is inserted together with the balloon catheter to a position immediately on the proximal side of a stenosed portion of the coronary artery, which portion is the target site. This is typically accomplished under fluoroscopic observation. Next, the distal end of the guide wire is passed through the stenosed portion. Thereafter, the balloon of the balloon catheter is guided to the stenosed portion while being maintained along the guide wire, and the balloon is dilated to dilate the stenosed portion, thereby securing a quantity of bloodstream.

For instance, in order to insert a guide wire from a femoral artery and to advance it through an aorta, an aortic arch and a coronary artery orifice into the coronary artery by the Seldinger technique, it is desirable that the guide wire exhibit excellent flexibility for following the track of the blood vessels (trackability) and pushability to help ensure effective transmission of a pushing force from the operator's hand side (the proximal side) to the distal part of the guide wire.

In addition, for the purpose of advancing the guide wire into a desired branch at a branching part of the coronary artery or the like, a distal part of the guide wire may in some cases be shaped in conformity with the shape of the branching part. Such a shaping operation is ordinarily performed with the surgeon's fingers at the time of surgery, and is called "reshaping".

Especially, in the case of inserting the distal end of a guide wire into the coronary artery on the peripheral side, it may in many cases be impossible to select the desired branch while using the preformed angle-type or J-type tip shape of known guide wires, and so it may be necessary to reshape the guide wire tip into a desired shape and then try to insert it into the coronary artery as desired. Also, when the shape of the guide wire tip is not satisfactory for the intended selection of the desired branch, it is necessary to remove the guide wire from the catheter, reshape the guide wire tip once again and insert the guide wire again.

There is known a guide wire in which a wire body is included of a Ni—Ti alloy exhibiting superelasticity, for obtaining flexibility at the distal part of the guide wire. In this case, however, the superelasticity of the distal part of the wire body makes the reshaping difficult. In view of this, there has been developed a guide wire having a reshapeable distal part as follows.

A guide wire in which a distal part of a core wire (wire body) composed of a superelastic alloy has had its superelasticity degraded by heat treatment is disclosed in, for example, U.S. Pat. No. 5,452,726.

However, in the case where the superelasticity of the distal part is degraded by heat treatment, the distal part provided easily with a new shape upon reshaping may return to its original shape by losing the new shape upon being inserted into a living body. This is because the superelastic alloy tends to return to its original straight shape due to its own shape memory effect. More specifically, the heat treatment raises the transformation temperature of the distal part, and the heat-treated part does not exhibit superelasticity at room temperature, so that this part can be shaped as if it were plastically deformed. However, the deformation in this instance is an apparent plastic deformation. Therefore, when the reshaped part is inserted into the living body and is warmed up to the body temperature, its transformation temperature is approached and it returns to the original straight shape.

Proposals have also been made for a guide wire in which the superelasticity of the distal part of a core wire (wire body) is deprived by cold drawing. An example is described in U.S. Pat. No. 5,238,004.

However, in the case where superelasticity is lost by cold drawing, the effect may often be unsatisfactory and so reshaping may be difficult to achieve. In addition, the worked part may become harder than required, thereby lowering the flexibility of the distal part of the guide wire. In order to enhance the flexibility, it may be contemplated to set a flat plate-like section (reshapeable section) to be thinner. In that case, however, the strength of the flat plate-like section cannot be maintained. Since the guide wire tip may be advanced through a stenosed portion while being rotated or may be pulled in a bent state, it must have a strength (e.g., tensile strength) not lower than a certain value. Therefore, there is a limit to the thinning of the flat plate-like section. Accordingly, by this approach it is quite difficult, if not impossible, to secure both flexibility and strength.

SUMMARY

A guide wire includes a wire body having a plate-like reshapeable section at a distal part thereof. According to one aspect, the guide wire may include a wire body having an elongate reshapeable section at a distal part of the wire body. The surface of the reshapeable section is provided with a plurality of grooves extending in a direction different from the longitudinal direction of the reshapeable section.

The reshapeable section can be plate-shaped and provided with the grooves in at least one side of the plate-shaped section. According to one alternative, the grooves are provided on opposite surfaces of the reshapeable section, and can be positioned in the same pattern on the opposite sides of the plate-shaped section or can be arranged in different patters on the two sides. The grooves on the opposite surfaces can be aligned or in staggered relation to one another in the longitudinal direction. The reshapeable section can be configured so that its thickness and/or width decreases, continuously or stepwise, in the distal direction.

The reshapeable section can also be bar-shaped, and provided with the grooves in the outside surface. The grooves may be formed in an annular shape or a spiral shape. The grooves can be provided in opposite surfaces of the bar-shaped reshapeable section, and can be positioned in the same pattern on the opposite sides of the section or can be arranged in different patters on the two sides. The grooves on the opposite surfaces can be aligned or in staggered relation to one another in the longitudinal direction. The reshapeable section can be configured so that its diameter decreases, continuously or stepwise, in the distal direction.

The grooves preferably are formed at intervals along the longitudinal direction of the reshapeable section. The interval between the adjacent grooves may decrease along the distal direction of the reshapeable section. The depth of the groove preferably increases or decreases along the distal direction of the reshapeable section. The width of the grooves may also increase or decrease along the distal direction of the reshapeable section. All or some of the grooves can be filled with a malleable metal. A part of the wire body, inclusive of the reshapeable section, is preferably made of a superelastic alloy. The wire body preferably has a tapered section of which the outer diameter gradually decreases in the distal direction. The tapered section is preferably formed on the distal side of and in the vicinity of the reshapeable section.

The guide wire preferably further includes a coil which covers the reshapeable section. The guide wire preferably further includes fixing materials for fixing the coil to the wire body at a plurality of locations, wherein one of the plurality of fixing materials is disposed on the distal side of the reshapeable section, and another of the plurality of fixing materials is disposed on the proximal side of the reshapeable section. The guide wire preferably further includes a resin coating layer which covers the coil. An outer peripheral surface of the resin coating layer preferably is provided with a groove at a portion corresponding to the reshapeable section.

According to another aspect, a guide wire comprises a wire body comprised of a plurality of sections including an elongate reshapeable section, an elongate constant diameter section and an elongate tapering section, wherein the constant diameter section has an outer diameter that is constant along an entirety of a longitudinal extent of the constant diameter section, wherein the tapering section has an outer diameter that tapers from a larger outer diameter to a smaller outer diameter toward the reshapeable section, wherein the constant outer diameter section and the tapering section both are positioned proximally of the reshapeable section, and wherein the elongate reshapeable section is made of a superelastic alloy and possesses an outer circumferential surface. In addition, a plurality of spaced apart grooves are formed in the outer circumferential surface of the reshapeable section, with each groove extending around less than half the outer circumferential surface of the reshapeable section, and each groove extending in a direction different from the longitudinal direction of the reshapeable section.

In accordance with another aspect, a guide wire comprises a wire body comprised of a proximal part and a distal part, where the distal part is located distally of the proximal part, an elongate reshapeable section provided at the distal part of the wire body, wherein the elongate reshapeable section is bar-shaped, possesses a circular cross-sectional shape, extends in a longitudinal direction and possesses an outer surface, and wherein the outer surface of the reshapeable section is provided with a spiral groove.

BRIEF DESCRIPTION OF THE DRAWING FIGURES

DETAILED DESCRIPTION

Figure 1:
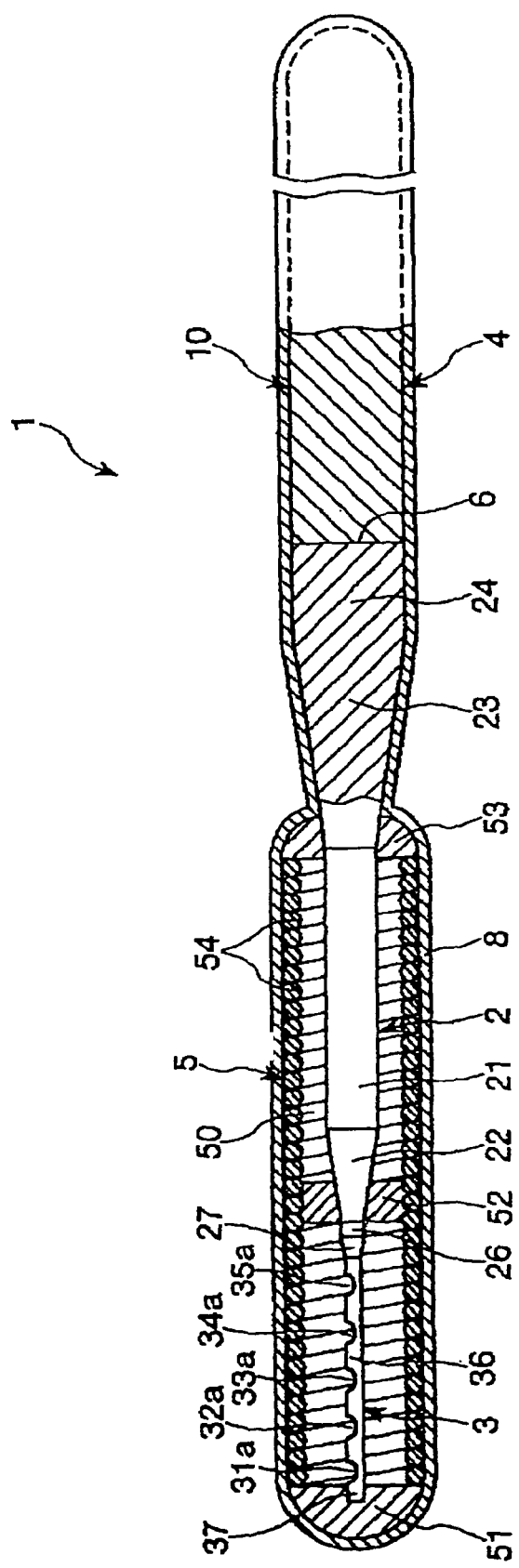
FIG. 1 is a partial longitudinal sectional view (schematic side view) of a first embodiment of the guide wire disclosed here.
Figure 2:
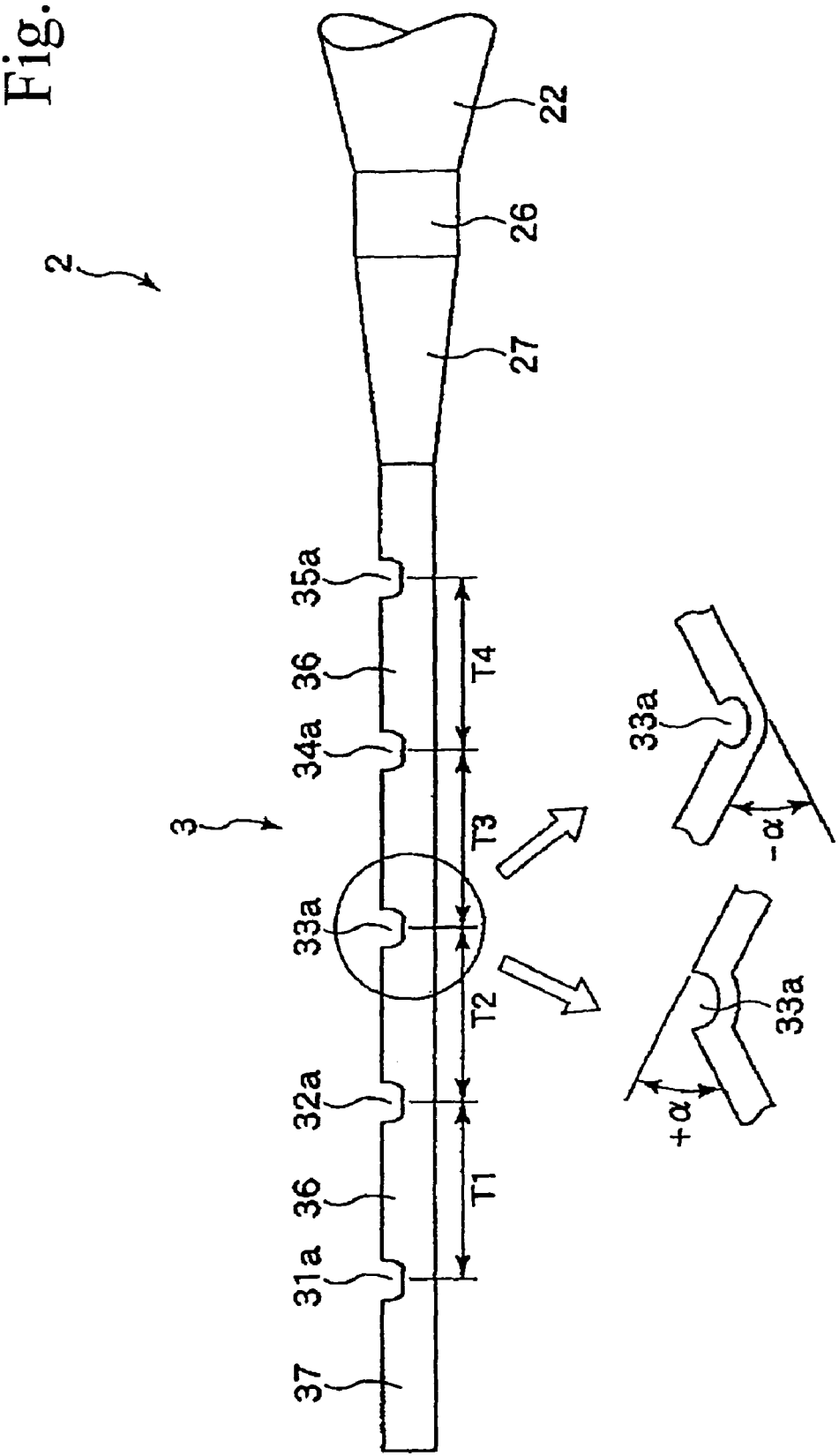
FIG. 2 is a side view of the reshapeable section of the guide wire shown in FIG. 1.
Figure 3:
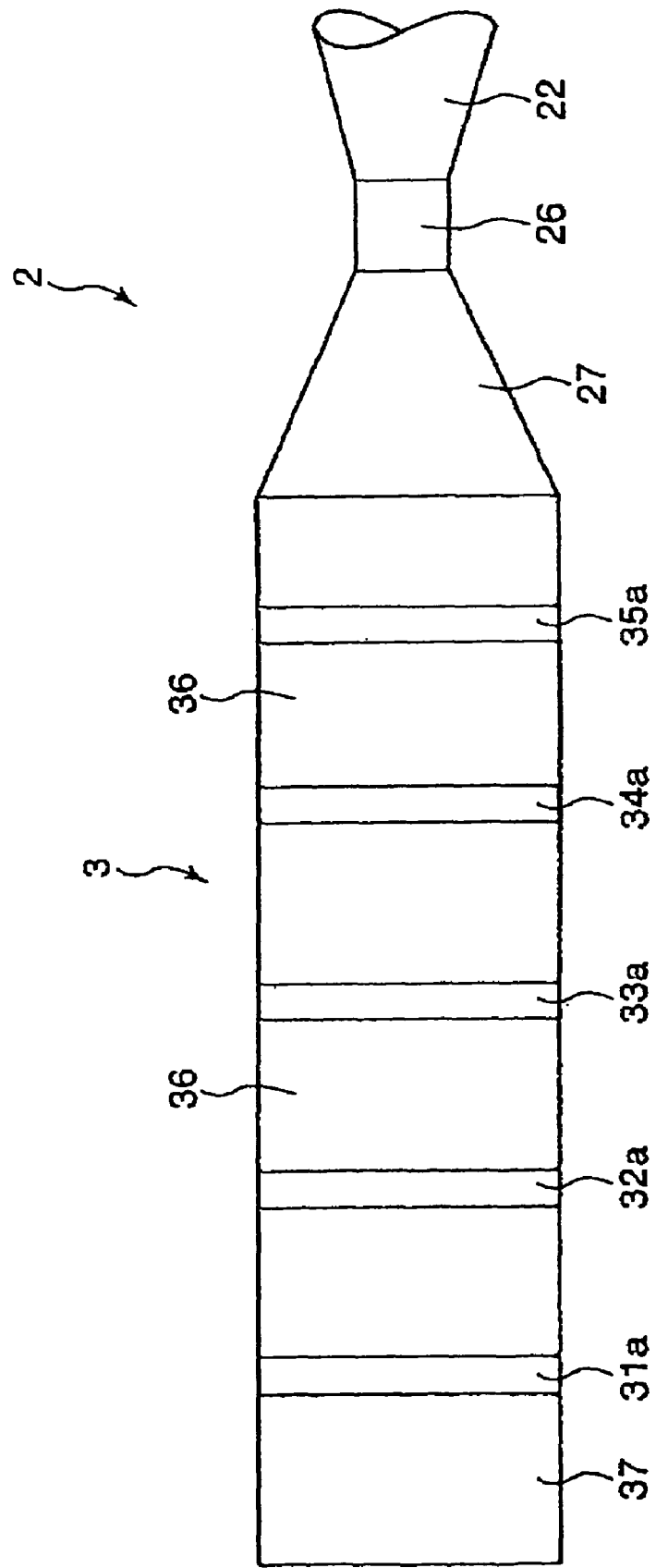
FIG. 3 is a plan view of the reshapeable section of the guide wire shown in FIG. 1.

One embodiment of a guide wire disclosed here is illustrated in FIGS. 1-3. For convenience in the description below, the right side in FIGS. 1-3 will be referred to as the proximal end or proximal side (or proximal direction), and the left side will be referred to as the distal end or distal side (or distal direction). In addition, the upper side in FIGS. 1 and 2 will be referred to as the upper side (or upper direction) and the lower side will be referred to as the lower side (or lower direction). In addition, to help facilitate an understanding, the guide wire in FIGS. 1-3 is schematically illustrated as being shortened in the longitudinal direction and exaggerated in the diametrical direction (thickness direction). Thus the ratio between the size in the longitudinal direction and the size in the diametrical direction in these drawings is different from the actual ratio. This same observation also applies to the other drawing figures herein (FIGS. 4-14).

The guide wire 1 shown in FIG. 1 is a catheter guide wire configured to be inserted in the lumen of a catheter (inclusive of endoscope), and includes a wire body 10 and a helical coil 5. The wire body 10 is constructed to include a first wire 2 disposed on the distal side and a second wire 4 disposed on the proximal side of the first wire 2, where the first and second wires 2, 4 are joined to each other. The helical coil 5 is disposed at the distal part (distal-side part) of the wire body 10. The overall length of the guide wire 1 is not particularly limited, though is preferably about 200 to 5000 mm.

The first wire 2 is fabricated of a wire material which is flexible or elastic. In the present embodiment, the first wire 2 is comprised of a plurality of sections including a constant outer diameter section 21, a first tapered section 22, a distal-side constant outer diameter section 26, a plate-like transition section 27, a reshapeable section 3, a large diameter section 24, and a second tapered section 23. The constant outer diameter section 21 possesses an outer diameter that is constant (inclusive of substantially constant). The first tapered section 22 is located on the distal side of the constant outer diameter section 21 and possesses an outer diameter that gradually decreases along the distal direction. The distal-side constant outer diameter section 26 is located on the distal side relative to the first tapered section 22 and possesses an outer diameter that is constant (inclusive of substantially constant). The plate-like transition section 27 is located on the distal side of the distal-side constant outer diameter section 26 and is configured to decrease in thickness and increase in width along the distal direction. The reshapeable section 3 is located on the distal side of the transition section 27. The large diameter section 24 is located on the proximal side relative to the constant outer diameter section 21, and possesses an outer diameter larger than the constant outer diameter section 21. The second tapered section 23 is located between the constant outer diameter section 21 and the large diameter section 24, and gradually decreases in outer diameter in the distal direction. The sections described above are sequentially disposed in the following order from the distal side of the first wire towards the proximal end—the reshapeable section 3, the transition section 27, the distal-side constant outer diameter section 26, the first tapered section 22, the constant outer diameter section 21, the second tapered section 23 and the large diameter section 24.

With the first tapered section 22 formed between the reshapeable section 3 and the constant outer diameter section 21, particularly with the reshapeable section 3 formed on the distal side of and in the vicinity of the first tapered section 22, the rigidity (flexural rigidity, torsional rigidity) of the first wire 2 is gradually reduced along the distal direction. As a result, the guide wire 1 is provided with a good crossability of stenosed portion and flexibility at a distal part thereof, whereby trackability along blood vessels and the like, and safety are enhanced, and kinking and the like are inhibited or prevented.

In a similar manner, with the second tapered section 23 disposed so that the constant outer diameter section 21 and the large diameter section 24 are connected through the second tapered section 23, the rigidity (flexural rigidity, torsional rigidity) of the first wire 2 is gradually decreased along the distal direction.

The taper angle (the rate of decrease in outer diameter) of the first tapered section 22 (also of the second tapered section 23) may be constant along the longitudinal direction of the wire body 10 or may vary along the longitudinal direction of at least a part of the first tapered section 22. For example, a plurality of portions having a comparatively larger taper angle (rate of decrease in outer diameter) and a plurality of portions having a comparatively smaller taper angle may be formed alternately and repeatedly.

Also, there may be differences in taper shape and/or taper angle, between the first tapered section 22 and the second tapered section 23.

The reshapeable section 3, constructed in the manner described below in more detail, is positioned on the distal side of the first tapered section 22, with the distal-side constant outer diameter section 26 and the transition section 27 positioned between the reshapeable section 3 and the first tapered section 22. The reshapeable section 3 is preferably integrally formed as a single body with the first tapered section 22. In this embodiment, the entirety of the first wire 2, inclusive of the reshapeable section 3, is integrally formed as one body of the same material. As will be described later, a preferable material constituting the first wire 2 is a superelastic alloy (an alloy exhibiting pseudo-elasticity) represented by Ni—Ti alloy. Therefore, a preferable material of the reshapeable section 3 is also a superelastic alloy, and such a construction as this will be described below.

As shown in FIGS. 2 and 3, the reshapeable section 3 is plate-shaped and is adapted to be used after it is deformed into a desired shape (after reshaping). Generally, a guide wire may in some cases be used after its distal part is preliminarily deformed by, for example, a surgeon into a desired shape, for the purpose of conforming the distal part of a catheter or the like to be guided to the shape of a blood vessel or for the purpose of achieving appropriate and smooth selection of and guide into a desired branch of blood vessel. The bending of the distal part of the guide wire into a desired shape in this manner is called "reshaping". With the reshapeable section 3 provided in the guide wire here, he reshaping can be carried out relatively easily and assuredly, whereby operationality (manipulability) in inserting the guide wire 1 into a living body is enhanced remarkably.

A portion of the outer circumferential surface of the plate-shaped reshapeable section 3 is provided with a plurality of grooves. In the illustrated embodiment, the upper surface of the reshapeable section 3 is provided with the grooves. These grooves extend in a direction different from the longitudinal direction or longitudinal extent of the reshapeable section 3 (in this embodiment, the extending direction is a direction orthogonal to the longitudinal direction of the reshapeable section 3, specifically, the extending direction is the width-wise direction of the reshapeable section 3). The grooves are also positioned at intervals along the longitudinal direction of the reshapeable section 3, meaning that adjacent-most grooves are spaced apart from one another along the longitudinal extent of the reshapeable section 3. More specifically, as shown in FIGS. 2 and 3, the reshapeable section 3 is provided with a total of five grooves 31a, 32a, 33a, 34a, 35a, in this order from the distal side.

In the reshapeable section 3, the portions where the grooves 31a-35a are formed (hereinafter referred to as "groove formed portions") are smaller in than the other portions (for example, the portions 36 between the adjacent grooves, and a portion 37 on the distal side relative to the distal-most groove 31a) in plate thickness of the reshapeable section 3. Stated differently, in the reshapeable section 3, the portions where the grooves 31a-35a are formed are smaller in cross-sectional area than the other portions of the reshapeable section 3. Therefore, when the reshapeable section 3 is reshaped, the groove formed portions are more susceptible to deformation (plastic deformation) than the other portions of the reshapeable section 3. Accordingly, the reshapeable section 3 can be reshaped into a desired shape relatively easily and assuredly, and the shape upon reshaping is maintained. The reshapeable section 3 thus reshaped into the desired shape keeps the shape upon reshaping, not only at normal temperature but also when its temperature is raised roughly to the body temperature of a person.

Since the reshapeable section 3 is provided partly with the grooves 31a-35a so as to render the groove formed portions susceptible to plastic deformation, it is possible to avoid the situation in which the reshapeable section 3 as a whole is hardened more than necessary in a manner lowering the flexibility or elasticity of the distal part of the guide wire 1. Furthermore, the reshapeable section 3 as a whole may be deprived of elasticity (be rendered susceptible to plastic deformation) by subjecting the reshapeable section 3 to a heat treatment.

The degree of plastic deformation of the grooves 31a-35a at the time of reshaping may be, for example, as follows. As shown in FIG. 2, let the bending angle when the portion near the groove 33a is bent into an "inverted V shape" in the direction of opening the groove 33a be $+\alpha°$, and let the bending angle when the portion near the groove 33a is bent into a "normal V shape" in the direction of closing the groove 33a be $-\alpha°$, and the same also being applicable to the other four grooves 31a, 32a, 34a, 35a. Then, the distal end of the reshapeable section 3 can be bent to an angle of $\pm 5\alpha°$ at maximum relative to the proximal end of the reshapeable section 3 by virtue of the bending of the total of the five grooves 31a-35a. For example, where $\alpha$ is 18°, the distal end of the reshapeable section 3 can be so bent as to be substantially perpendicular to the proximal end of the reshapeable section 3 (the reshapeable section 3 can be bent into a L shape) because each of the grooves 31a-35a would permit a bend of 18° (18°×5=90°). In addition, where $\alpha$ is 36°, the distal end of the reshapeable section 3 can be bent back upon itself so as to extend in the reverse direction (a 180° bend) toward the proximal end of the reshapeable section 3. The reshapeable section 3 would thus be bent into U shape. The value of a can be adjusted, as desired, by appropriately selecting the shapes and dimensions (length, width, depth, etc.) of the grooves 31a-35a, the number of the grooves formed, the pattern in which the grooves are formed, and other relevant conditions.

The shape of the reshapeable section 3 upon reshaping is not limited to the L shape and the U shape (J shape), and may be any of a variety of other shapes such as S shape and three-dimensional shapes. If the intervals between the adjacent ones of the grooves 31a-35a in the reshapeable section 3 are represented by T1, T2, T3, T4 respectively as shown in FIG. 2, the values of T1, T2, T3, T4 are equal (inclusive of substantially equal) in the illustrated embodiment of FIG. 2. In other words, the grooves 31a-35a are formed at a fixed pitch or equal intervals along the longitudinal direction of the reshapeable section 3. However, it is to be understood that the intervals T1, T2, T3, T4 between the adjacent grooves may all be different from one another, or some of the intervals may be different from the others.

Examples of the just-mentioned configuration include the case where the interval between the adjacent grooves decreases in the distal direction in some part of the reshapeable section 3. For example, the intervals T1, 12, T3, T4 satisfy the relationship T1≦T2≦T3≦T4 (exclusive of the case of T1=T2=T3=T4). Such a configuration permits the reshapeable section 3 to be reshaped more finely as the distal end is approached, which naturally is preferable. In other words, since the density of the grooves formed in the reshapeable section 3 is higher on the distal side than on the proximal side, the reshapeable section 3 can be reshaped into a more complicated shape or finer shape (for example, into a more acutely curved or bent shape) on the distal side than on the proximal side.

The practical values of T1, T2, T3, T4 are preferably about 0.1 to 2 mm, more preferably about 0.5 to 1 mm.

In the configuration shown in FIG. 2, the depths of the grooves 31a-35a in the reshapeable section 3 are substantially equal. However, it is also possible that the depths of the grooves 31a-35a may all be different from one another, or the depth of some of the grooves may be different from the others.

Examples of the just-mentioned configuration include the case where the groove depth increases (or decreases) in the distal direction in some part of the reshapeable section 3. For example, the depths D1, D2, D3, D4, D5 of the grooves 31a, 32a, 33a, 34a, 35a respectively satisfy the relationship D1≧D2≧D3≧D4≧D5 (exclusive of the case of D1=D2=D3=D4=D5). Such a configuration permits the reshapeable section 3 to be bent at sharper angles (more acutely) and be reshaped more finely, as the distal end is approached, which naturally is preferable. In other words, the reshapeable section 3 can be reshaped into a more complicated shape or finer shape (particularly, a more acutely curved or bent shape) on the distal side than on the proximal side.

In addition, a configuration may be adopted in which, contrary to the above configuration, the groove depth decreases in the distal direction in some part of the reshapeable section 3. For example, the depths of the grooves satisfy the relationship D1≦D2≦D3≦D4≦D5 (exclusive of the case of D1=D2=D3=D4=D5).

The practical values of D1, D2, D3, D4 and D5 are preferably about 0.001 to 0.03 mm, more preferably about 0.003 to 0.01 mm.

In the FIG. 2 embodiment, the widths of the grooves 31a-35a in the reshapeable section 3 are substantially equal. However, this may be altered in that the widths of the grooves 31a-35a may all be different, or the widths of some of the grooves may be different from the others.

Examples of the just-mentioned configuration include the case where the groove width increases (or decreases) in the distal direction in some part of the reshapeable section 3. For example, the widths W1, W2, W3, W4, W5 of the grooves 31a, 32a, 33a, 34a, 35a satisfy the relationship W1≧W2≧W3≧W4≧W5 (exclusive of the case of W1=W2=W3=W4=W5). Such a configuration permits the reshapeable section 3 to be bent at sharper angles (more acutely) and be reshaped more finely, as the distal end is approached, which naturally is preferable. In other words, the reshapeable section 3 can be reshaped into a more complicated shape or finer shape (particularly, a more acutely curved or bent shape) on the distal side than on the proximal side.

In addition, in the present invention, a configuration may be adopted in which, contrary to the above configuration, the groove width decreases in the distal direction in some part of the reshapeable section 3. For example, the widths of the grooves satisfy the relationship W1≦W2≦W3≦W4≦W5 (exclusive of the case of W1=W2=W3=W4=W5).

The width of each of the grooves 31a-35a may be constant along the longitudinal direction of the groove, or may vary in some intermediate part. For example, each of the grooves 31a-35a may be configured so that the groove width is larger (or smaller) at both end parts thereof (near edges of the reshapeable section 3) than in a central part of the reshapeable section 3.

The practical values of W1, W2, W3, W4 and W5 are preferably about 0.06 to 0.5 mm, more preferably about 0.1 to 0.4 mm.

In addition, the cross-sectional shape of each of the grooves 31a-35a is not particularly limited, and may be any shape. Examples include U-shape grooves (grooves of arcuate shape), V-shape grooves, W-shape grooves, rectangular shape grooves, or pentagonal shape grooves.

In the present embodiment, the width of the reshapeable section 3 is substantially uniform along the longitudinal direction. Specifically, at least the portions of the plate-shaped reshapeable section 3 including the grooves 31a-35a (groove formed portions) are substantially constant in width. The value of the width of the reshapeable section 3 is not particularly limited, insofar as the reshapeable section 3 can be contained in the inside space (gap 50) of the coil 5. In order to secure sufficient flexibility and appropriate strength, however, the width of the plate-shaped reshapeable section 3 is preferably about 0.1 to 0.5 mm, more preferably about 0.15 to 0.35 mm.

This embodiment is not limited to the configuration in which the width of the plate-shaped reshapeable section 3 is uniform along the longitudinal direction. The plate may vary in some intermediate part of the reshapeable section 3. For example, the groove formed portions of one or more of the grooves 31a-35a (preferably, all of the grooves) may have an increased or decreased width, as compared with portions other than the grooves of the reshapeable section 3 (for example, the straight portions 36 between the adjacent grooves, or the portion 37 on the distal side of the groove 31a).

In the present embodiment, the thickness of the plate-shaped reshapeable section 3 (the thickness of the portions excluding the grooves 31a-35a) is substantially uniform along the longitudinal extent of the reshapeable section 3. The value of the thickness of the reshapeable section 3 is not particularly limited. In order to secure sufficient flexibility and appropriate strength, however, the thickness is preferably about 0.01 to 0.06 mm, more preferably about 0.02 to 0.04 mm.

While the grooves 31a-35a are formed, preferably evenly formed, throughout the whole length of the reshapeable section 3 in the illustrated embodiment, the guide wire is not necessarily limited in this regard. A plurality of grooves may be formed along only a portion of the longitudinal extent of the reshapeable section 3. Examples of such a configuration include a configuration in which the grooves 34a, 35a in FIGS. 2 and 3 are omitted, and the grooves 31a, 32a, 33a are formed only in an intermediate part and a distal part of the reshapeable section 3.

In addition, while the grooves 31a-35a are straight in plan-view shape as shown in FIG. 3, this configuration is not limitative. At least one of the grooves 31a-35a may have a plan-view shape of a polygonal line such as V-shape, W-shape, etc. or a curved line such as arcuate shape, S-shape, etc.

Furthermore, other arbitrary groove(s) through which two or more of the grooves 31a-35a communicate with each other may be provided.

While both edge parts of each of the grooves 31a-35a in the reshapeable section 3 are sharply shaped, the guide wire is not necessarily limited in this respect. For example, both edge parts of each of the grooves 31a-35a may be rounded in shape.

In the first wire 2, each of the distal-side constant outer diameter section 26, the constant outer diameter section 21 and the large diameter section 24 has a constant outer diameter along the longitudinal direction of the wire. The outer diameter of the distal-side constant outer diameter section 26 is equal (inclusive of substantially equal) to the minimum outer diameter of the first tapered section 22, and the outer diameter of the constant outer diameter section 21 is equal (inclusive of substantially equal) to the maximum outer diameter of the first tapered section 22 and is equal (inclusive of substantially equal) to the minimum outer diameter of the second tapered section 23. Also, the outer diameter of the large diameter section 24 is equal (inclusive of substantially equal) to the maximum outer diameter of the second tapered section 23.

The distal end of the second wire 4 is joined to the proximal end of the first wire 2 (the proximal end of the large diameter section 24). The second wire 4 is fabricated of a flexible or elastic wire material.

The method of joining the first wire 2 and the second wire 4 is not particularly limited. Examples of the joining method include welding such as friction welding, welding using a laser, butt resistance welding, e.g., upset welding, etc., and joining by use of a tubular joint member. Among these joining methods, butt resistance welding is particularly preferred since it can be carried out comparatively easily and it provides a high joint strength.

In the present embodiment, the second wire 4 is substantially constant in outer diameter. The outer diameter of the second wire 4 is substantially equal to the outer diameter of the large diameter section 24 of the first wire 2. This helps ensure that when the proximal end of the large diameter section 24 of the first wire 2 and the distal end of the second wire 4 are joined to each other, any step due to a difference in outer diameter between the wires 2, 4 is not generated but a continuous surface can be obtained, at the outer periphery of the joint part (weld part) 6 of the wires 2, 4. It is to be understood though that this structure is not limitative. For example, the outer diameter(s) of the first wire 2 and/or the second wire 4 may vary across the joint part 6.

The materials constituting the first wire 2 and the second wire 4 are not particularly limited. Examples of the materials which can be used here include various metallic materials such as stainless steels (all species of SUS, e.g., SUS304, SUS303, SUS316, SUS316L, SUS316J1, SUS316J1L, SUS405, SUS430, SUS434, SUS444, SUS429, SUS430F, SUS302), piano wire, cobalt alloys, pseudo-elastic alloys (inclusive of superelastic alloys), etc.

The material constituting the first wire 2 is preferably a pseudo-elastic alloy (inclusive of superelastic alloy), more preferably a superelastic alloy.

Superelastic alloys are rich in flexibility, have a restoring property, and have little tendency to undergo irreversible bending. Therefore, with the first wire 2 included of a superelastic alloy, the guide wire 1 can have sufficient flexibility and restoring property on bending, is enhanced in trackability with respect to complicatedly curved or bent blood vessels and the like, and can show more excellent operationality. In addition, even when the first wire 2 is subjected repeatedly to curving or bending deformations, the restoring property possessed by the first wire 2 inhibits or prevents the first wire 2 from tending to undergo irreversible bending, so that it is possible to reduce or prevent the operationality of the guide wire 1 from being lowered due to a tendency to undergo irreversible bending acquired by the first wire 2 during the use of the guide wire 1.

Possible elastic (superelastic) metals which can be utilized include those elastic metals whose stress-distortion curve by tension has a variety of shapes, and also those elastic metals whose transformation temperature such as As (austenite start temperature), Af (austenite finish temperature), Ms (martensite start temperature), and Mf (martensite finish temperature) can or cannot be measured. Further, all of those superelastic metals which are deformed (distorted) by a relatively great amount by stress and return to their original shape in response to removal of the stress are included. Thus, superelastic alloys includes those which exhibit different tensile stress vs. strain curves (i.e., the superelastic alloys which can be used here are not limited to superelastic alloys having a particular tensile stress vs. strain curve), those which have transformation points such as As, Af, Ms, Mf, whether they are clearly measurable or not, and those which are largely deformed (strained) under stresses and return to their original shape upon removal of the stresses.

Examples of the preferable composition of the superelastic alloy include NiTi alloys such as a Ni—Ti alloy containing 49 to 52 at. % of Ni, Cu—Zn alloys containing 38.5 to 41.5 wt. % of Zn, and Cu—Zn—X alloys containing 1 to 10 wt. % of X (X is at least one selected from among Be, Si, Sn, Al and Ga), and Ni—Al alloys containing 36 to 38 at. % of Al. Among these, particularly preferred are the Ni—Ti alloys. Incidentally, the superelastic alloys represented by the Ni—Ti alloys are excellent also in adhesion of a resin coating layer 8 which will be described later.

Cobalt alloys each show a high modulus of elasticity when formed into wires, and each have an appropriate elastic modulus. Therefore, a wire included of a cobalt alloy is excellent in torque transmission performance, and is extremely insusceptible to such problems as buckling. The cobalt alloy to be used here may be any alloy that contains Co as a constituent element; however, alloys containing Co as a main constituent (Co-based alloys, namely, alloys in which the content of Co by weight is the highest of the contents of constituent elements) are preferred, and Co—Ni—Cr alloys are more preferred. When an alloy with such a composition is used, the above-mentioned effect becomes more conspicuous. In addition, an alloy with such a composition has a high modulus of elasticity, and can be cold deformed notwithstanding that the elastic limit is set to be high. The high elastic limit makes it possible to reduce the wire diameter while sufficiently preventing generation of buckling, and therefore to obtain a guide wire having rigidity and flexibility sufficient for insertion to a desired site.

As the material constituting the second wire 4, the above-mentioned stainless steels are preferable. Stainless steels are higher in strength and rigidity than the above-mentioned superelastic alloys, and can therefore provide the guide wire 1 with excellent pushability and torque transmission performance.

The first wire 2 and the second wire 4 may be fabricated of different materials, or may be fabricated of the same metallic material or of metallic materials of the same type (alloys which contain the same main metallic elements). In the latter case, the joint part (weld part) 6 has a higher joint strength, so that even when the outer diameter of the joint part 6 is relatively small, disconnection or the like is inhibited or prevented and a good torque transmission performance and the like are displayed.

In the case where the first wire 2 and the second wire 4 are made of different materials, the first wire 2 is preferably fabricated of the above-mentioned superelastic alloy, more preferably a Ni—Ti alloy, while the second wire 4 is preferably comprised of the above-mentioned stainless steel.

The above description mentions that the first wire 2 and the second wire 4 are joined to each other. However, it is also possible for the guide wire to be composed of a single continuous wire body which is free of a joint part. In that case, examples of the material constituting the wire body include the same materials as above-mentioned, among which particularly preferred are the stainless steels, the cobalt alloys, and the pseudo-elastic alloys.

Around the outer periphery of a distal part of the wire body 10, a coil 5 is disposed so as to cover the distal part. With the coil 5 thus arranged, the area of contact of the wire body 10 with the inside wall of a catheter or the surface of a living body is reduced, whereby frictional resistance can be lowered. As a result, the guide wire 1 is further enhanced in operationality.

As shown in FIG. 1, the wire body 10 is inserted or located in a central part of the inside of the coil 5 (i.e., the coil 5 and the wire body 10 are coaxial). In the present embodiment, the reshapeable section 3, the transition section 27, the distal-side constant outer diameter section 26, the first tapered section 22, the whole part or part of the constant outer diameter section 21 are covered with the coil 5.

In addition, a distal part of the wire body 10 (particularly, the region ranging from the reshapeable section 3 to the first tapered section 22) is positioned relative to the coil 5 such that the inside surface of the wire body 10 is out of contact with the inside surface of the coil 5. This results in a gap 50 between the coil 5 and the distal part of the wire body 10.

The coil 5 is obtained by helically forming a filament 54 which is circular in cross-sectional shape. In this case, the coil 5 may be composed of a single filament 54 wound helically or of a plurality of filaments 54 wound helically.

The material constituting the filament 54 is not particularly limited. Examples of materials for filament 54 include a metallic material or a resin material. Examples of the metallic material include stainless steel, and radiopaque materials such as noble metals including Au, PT and the like, alloys contains those noble metals such as Pt—Ni alloys. In the latter case, radiopaqueness can be obtained at the distal part of the guide wire 1, and the guide wire 1 can be inserted into a living body while checking the position of the distal part under fluoroscopic observation, which naturally is preferable.

The coil 5 may be obtained by combining two or more materials. For example, a configuration may be adopted in which the filament 5 on the distal side of the coil 5 is made of a radiopaque material such as a Pt—Ni alloy whereas the filament 54 on the proximal side of the coil 5 is made of stainless steel. In this case, under fluoroscopic observation, the portion located on the distal side of the coil 5 (particularly, the portion including the reshapeable section 3) can be exaggerated (can be visually checked more easily) as compared with the portion located on the proximal side thereof; therefore, the position of the distal most portion of the guide wire 1 (the portion where the reshapeable section 3 is present) can be visually checked more clearly.

In addition, the guide wire disclosed here is not necessarily limited to the configuration in which the portion ranging from the reshapeable section 3 to the constant outer diameter section 21 is covered with the coil 5. For example, the reshapeable section 3, the transition section 27, the distal-side constant outer diameter section 26, the first tapered section 22 and the constant outer diameter section 21 may be partly covered with the coil 5. In that case, it is preferable that at least the outer periphery of the reshapeable section 3 is covered with the coil 5.

Where the coil 5 is arranged around the outer periphery of the reshapeable section 3, the coil 5 may be touching or in secure contact with the reshapeable section 3. In addition, such a coil 5 may be disposed for the purpose of imparting radiopaqueness to that portion of the guide wire 1 where the reshapeable section 3 is present.

In addition, the wire diameter of the filament 54 of the coil 5 may be uniform throughout the whole length of the coil 5, or may have different values respectively on the distal side and on the proximal side of the coil 5. For example, the wire diameter of the filament 54 on the distal side of the coil 5 may be smaller (or larger) than that on the proximal side. This makes it possible to further enhance the flexibility of the guide wire 1 at a distal part of the coil 5.

Besides, the outer diameter of the coil 5 may be constant over the whole length of the coil 5, or may have different values respectively on the distal side and on the proximal side of the coil 5. For example, the outer diameter of the coil 5 on the distal side of the coil 5 may be smaller than that on the proximal side. This makes it possible to further enhance the flexibility of the guide wire 1 at a distal part of the coil 5.

In the present embodiment, the adjacent turns of the filament 54 of the coil 5 are in contact with each other in the absence of an externally applied force, i.e., the coil 5 is in the state of the so-called close (tight) winding. The adjacent turns of the filament 54 exert a pressing force (compressive force) on each other in the axial direction of the wire body 10 in their natural condition. Here, the term "natural condition" means the condition where no external force is exerted. It is to be noted here, however, that the guide wire is not limited in this regard in that the adjacent turns of the filament 54 of the coil 5 may be spaced from each other in some part(s) of the coil 5.

As shown in FIG. 1, the coil 5 is fixed to the wire body 10 at a plurality of locations. In the illustrated embodiment, the coil 5 is fixed to the wire body 10 at three locations. Specifically, a distal part of the coil 5 is fixed to the distal end of the first wire 2 (the distal end of the reshapeable section 3) by a fixing material (fixing part) 51, a proximal part of the coil 5 is fixed to an intermediate part (in the vicinity of the boundary between the constant outer diameter section 21 and the second tapered section 23) of the first wire 2 by a fixing material (fixing part) 53, and an intermediate part of the coil 5 is fixed to the first tapered section 22 of the first wire 2 by a fixing material (fixing part) 52. With the coil 5 fixed at such locations, parts of the coil 5 can be securely fixed to the wire body 10, without spoiling the flexibility of a distal part (the part where the coil 5 is present) of the guide wire 1.

Particularly, since the reshapeable section 3 is fixed on the distal side (distal part) and the proximal side by the fixing materials 51, 52, the reshapeable section 3 can be assuredly fixed to the coil 5, so that the shape upon reshaping of the reshapeable section 3 can be maintained appropriately.

The fixing materials 51, 52, 53 are each preferably a solder material (brazing filler metal). However, the fixing materials 51, 52, 53 are not limited to a solder, but may be, for example, an adhesive. In addition, the method of fixing the coil 5 to the wire body 10 is not limited to the use of the fixing material(s) as welding may be used, for example. The distal end surface of the fixing material 51 is preferably rounded as shown in FIG. 1 in order to avoid the possibility of damaging the inside wall of a body lumen such as a blood vessel.

While the fixing material 52 is disposed on the first tapered section 22 in the configuration shown in the figure, this configuration is not limitative. The fixing material 52 may be disposed at any intermediate portion of the coil 5, provided the portion is located on the proximal side of the reshapeable section 3.

As shown in FIG. 1, the outside surface of the guide wire 1 is provided with a resin coating layer 8 covering the entirety (or a part) of the guide wire. The resin coating layer 8 may be formed for any of various purposes. An example of the various purposes is to reduce the friction (sliding resistance) of the guide wire 1 and to enhance slidability, thereby enhancing the operationality of the guide wire 1.

In order to reduce the friction (sliding resistance) of the guide wire 1, the resin coating layer 8 is preferably made of a material capable of reducing friction as described below. This helps ensure that the frictional resistance (sliding resistance) between the guide wire 1 and the inside wall of a catheter used therewith is reduced, and the slidability of the guide wire 1 is enhanced, whereby the operational characteristics of the guide wire 1 in the catheter are improved. In addition, reducing the sliding resistance of the guide wire 1 helps ensure that when the guide wire 1 is moved and/or rotated in a catheter, it is possible to more securely prevent the guide wire 1 from kinking (sharp bending) or becoming plastically damaged by torsional force, particularly to more assuredly inhibit or prevent a guide wire portion near the joint part 6 from kinking or becoming plastically damaged by torsional force.

Examples of materials capable of reducing the friction include polyolefins such as polyethylene, polypropylene, etc., polyvinyl chloride, polyesters (PET, PBT, etc.), polyamides, polyimides, polyurethane, polystyrene, polycarbonate, silicone resins, fluororesins (PTFE, ETFE, etc.), and composite materials of these.

The resin coating layer 8 may also be formed for the purpose of enhancing safety in inserting the guide wire 1 into a blood vessel or the like. For this purpose, the resin coating material 8 is preferably made of a material rich in flexibility (soft material, elastic material).

Examples of materials rich in flexibility include polyolefins such as polyethylene, polypropylene, etc., polyvinyl chloride, polyesters (PET, PBT, etc.), polyamides, polyimides, polyurethane, polystyrene, silicone resins, thermoplastic elastomers such as urethane elastomers, polyester elastomers, polyamide elastomers, etc., various rubber materials such as latex rubbers, silicone rubbers, etc., and composite materials obtained by combining two or more of these.

The resin coating layer 8 may not necessarily be made wholly of the same material. That is, different materials may be used respectively on the distal side and on the proximal side of an intermediate part of the guide wire 1. For example, a configuration may be adopted in which the portion of the resin coating layer 8 covering the first wire 2 and the coil 5 is made of the above-mentioned material rich in flexibility, whereas the portion of the resin coating layer 8 covering the second wire 4 is made of the above-mentioned material capable of reducing friction.

In addition, the resin coating layer 8 may be a single layer or a laminate of two or more layers (for example, a laminate in which an inner layer is included of a material softer than the material constituting an outer layer). For example, a configuration may be adopted in which the portion of the resin coating layer 8 covering the first wire 2 and the coil 5 is a single layer, whereas the portion of the resin coating layer 8 covering the second wire 4 is a laminate of two or more layers, or vice versa.

The outer peripheral surface of the resin coating layer 8 as above may be provided with a groove or grooves. Particularly, it is preferable that at least the portion of the resin coating layer 8 (the outer peripheral portion of the reshapeable section 3) corresponding to the reshapeable section 3 is provided with a groove or grooves in such a pattern as rectilinear shape, curved line shape, ring-like shape, spiral shape, net-like shape, etc. With such a groove or grooves, the flexibility of a distal part of the guide wire 1 is increased, and it is possible to reduce friction (sliding resistance) on the guide wire 1 and to further enhance slidability of the guide wire.

The outside surface of at least a distal part of the guide wire 1 is preferably coated with a hydrophilic material. This helps ensure that the hydrophilic material when wetted exhibits lubricity, whereby the friction (sliding resistance) of the guide wire 1 is reduced and the slidability of the guide wire 1 is enhanced. As a result, the operationality of the guide wire 1 is enhanced.

Examples of hydrophilic materials include cellulose polymeric materials, polyethylene oxide polymeric materials, maleic anhydride polymeric materials (for example, a maleic anhydride copolymer such as methyl vinyl ether-maleic anhydride copolymer), acrylamide polymeric materials (for example, polyacrylamide, polyglycidyl methacrylate-dimethyl acrylamide (PGMA-DMAA) block copolymer), water-soluble nylon, polyvinyl alcohol, and polyvinyl pyrrolidone.

Such hydrophilic materials, in many cases, exhibit lubricity through wetting (absorption of water), thereby reducing the frictional resistance (sliding resistance) between the guide wire 1 and the inside wall of a catheter used therewith. As a result, the slidability of the guide wire 1 is enhanced, and the operationality of the guide wire 1 in the catheter will be better.

Figure 4:
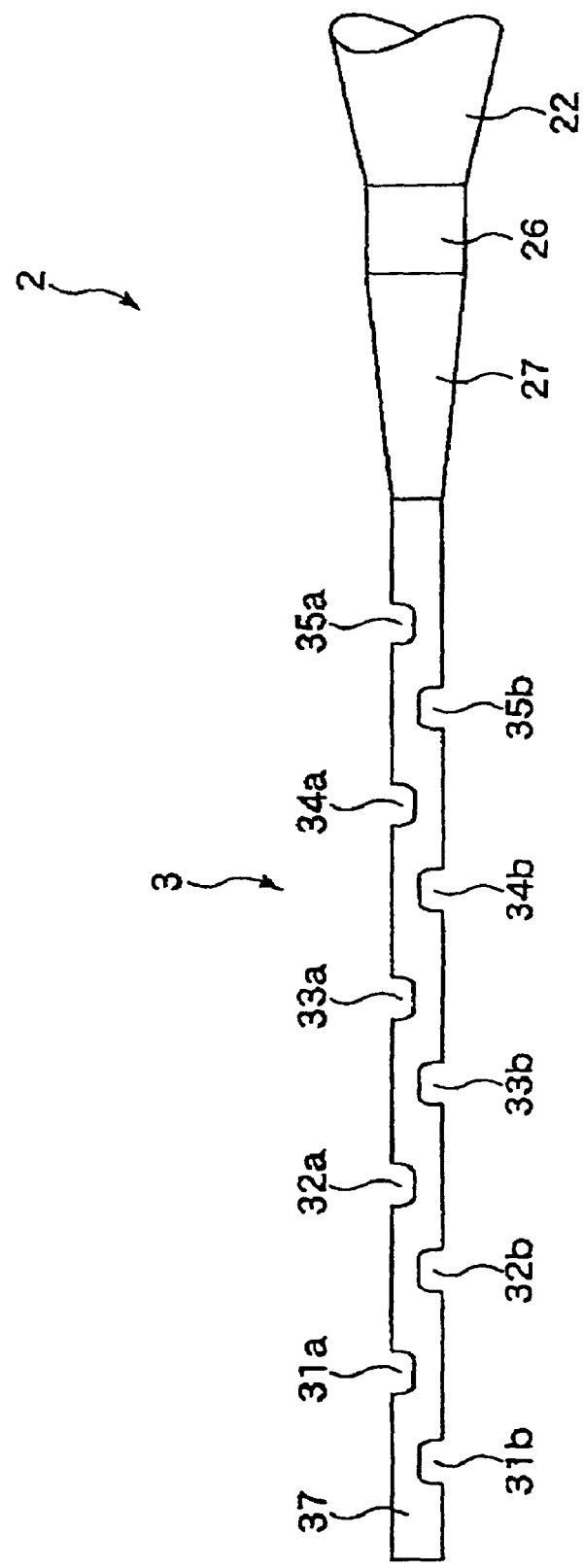
FIG. 4 is a side view of a reshapeable section according to a second embodiment of the guide wire disclosed here.
Figure 5:
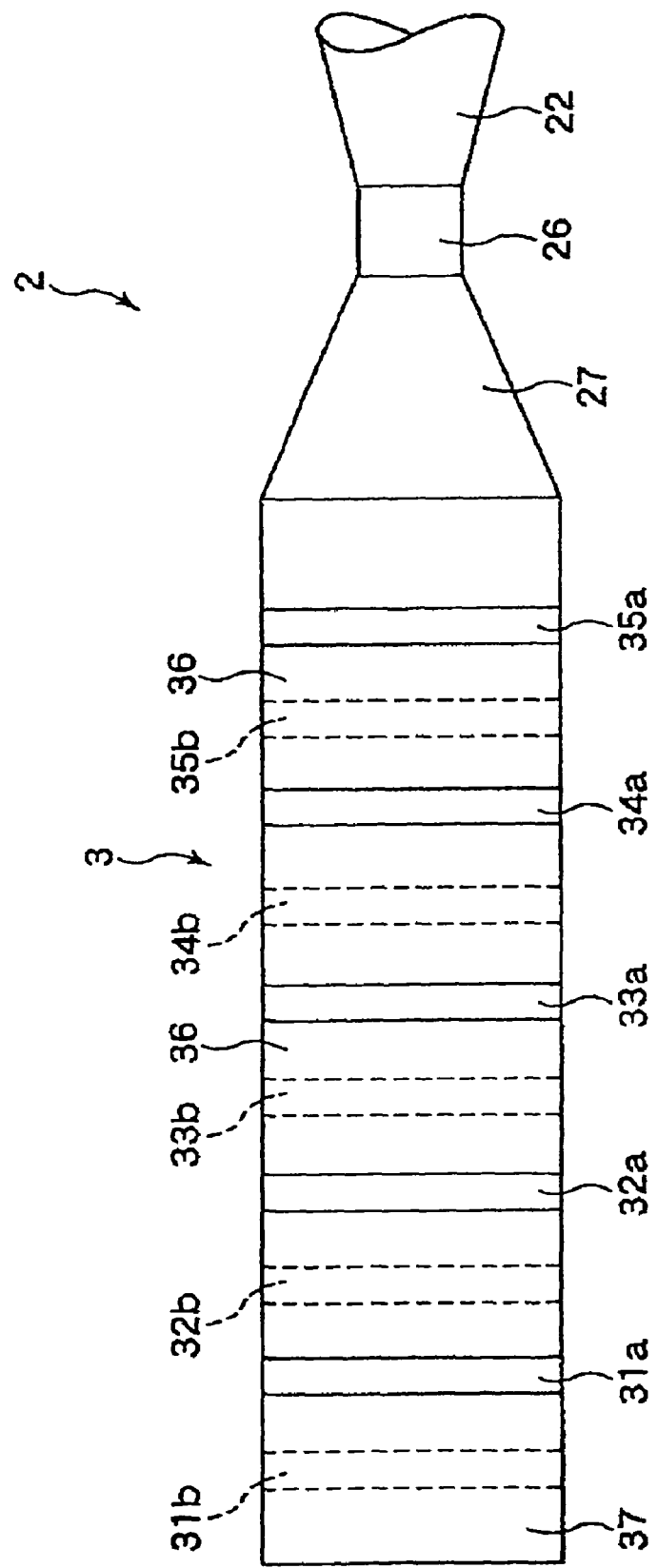
FIG. 5 is a plan view of the reshapeable section in the second embodiment of the guide wire.

FIGS. 4 and 5 illustrate a reshapeable section of a guide wire according to a second embodiment. The following description will primarily describe aspects of the second embodiment of the guide wire which differ from the first embodiment described above. Features in the second embodiment of the guide wire that are the same as or similar to those in the first embodiment are identified by the same reference numerals used in the first embodiment, and a detailed description of such features is not repeated.

For convenience of description, the right side in FIGS. 4 and 5 will be referred to as the proximal side or proximal end (proximal direction), the left side will be referred to as the distal end or distal side (or distal direction), the upper side will be referred to as the upper side (or upper direction) and the lower side will be referred to as the lower side (or lower direction).

This second embodiment of the guide wire is the same as the first embodiment above, except the configuration of the reshapeable section 3 is different.

As shown in FIGS. 4 and 5, the reshapeable section 3 is plate-shaped, and is provided with grooves similar to the grooves described above in the first embodiment. However, in this second embodiment, the grooves are positioned on both opposite sides of the plate-shapes reshapeable section 3 (the upper surface and the lower surface). The grooves formed in the upper surface (upper side) of the reshapeable section 3 and the grooves formed in the lower surface (lower side) may be arranged in the same pattern or in different patterns. In this embodiment, the grooves are arranged in different patterns.

To be more specific, in the present embodiment, five grooves 31a, 32a, 33a, 34a, 35a that are the same as those described above in the first embodiment are formed in the upper surface of the reshapeable section 3, and five grooves 31b, 32b, 33b, 34b, 35b are formed in the lower surface of the reshapeable section 3. In this case, the grooves 31a-35a formed in the upper surface of the reshapeable section 3 and the grooves 31b-35b formed in the lower surface of the reshapeable section 3 are formed alternately along the longitudinal direction of the reshapeable section 3. That is, the grooves 31a-35a and the grooves 31b-35b are arranged in a staggered pattern of half their pitch along the longitudinal direction of the reshapeable section 3. Thus, by way of example, the distance between the grooves 31b and 31a as measured along the longitudinal direction of the guide wire is one-half the distance between the grooves 31a and 32a (and one-half the distance between the grooves 31b and 32b). The characteristics of the grooves 31a-35a such as their shapes, dimensions, intervals, etc. are the same as or similar to those described above with respect to the grooves 31a-35a in the first embodiment, and so a detailed description of such characteristics is not repeated here.

The configuration described above and shown in FIGS. 4 and 5 helps ensure that any portion of the reshapeable section 3 in the longitudinal direction of the reshapeable section 3 can be bent (deformed) to the upper side and the lower side freely and into a fine shape, so that the reshapeable section 3 can wholly or partly be reshaped into a fine shape.

The grooves 31a-35a in the upper surface of the reshapeable section 3 and the grooves 31b-35b in the lower surface of the reshapeable section 3 may be the same or different in pattern, shape, dimensions (groove length, width, depth, etc.), intervals (pitch) and the like. For example, the grooves 31a-35a and the corresponding grooves 31b-35b may be provided at the same locations in the longitudinal direction of the reshapeable section 3.

In addition, while the grooves 31a-35a and the grooves 31b-35b are positioned (positioned substantially evenly) over substantially the whole length of the reshapeable section 3, this arrangement is not necessarily required. For example, a part of the lower surface (or the upper surface) of the reshapeable section 3, along the longitudinal extent of the reshapeable section 3, may be provided with one groove or a plurality of grooves. Examples of such an arrangement include a configuration in which, of the grooves 31b-35b in FIGS. 4 and 5, the grooves 34b, 35b are omitted, and the grooves 31b, 32b, 33b are only formed in an intermediate part and a distal part of the reshapeable section 3. In this case, the density of the grooves formed in the reshapeable section 3 is higher on the distal side than on the proximal side, so that the reshapeable section 3 can be reshaped into a more complicated shape or finer shape (for example, a more acutely curved or bent shape) on the distal side than on the proximal side.

Figure 6:
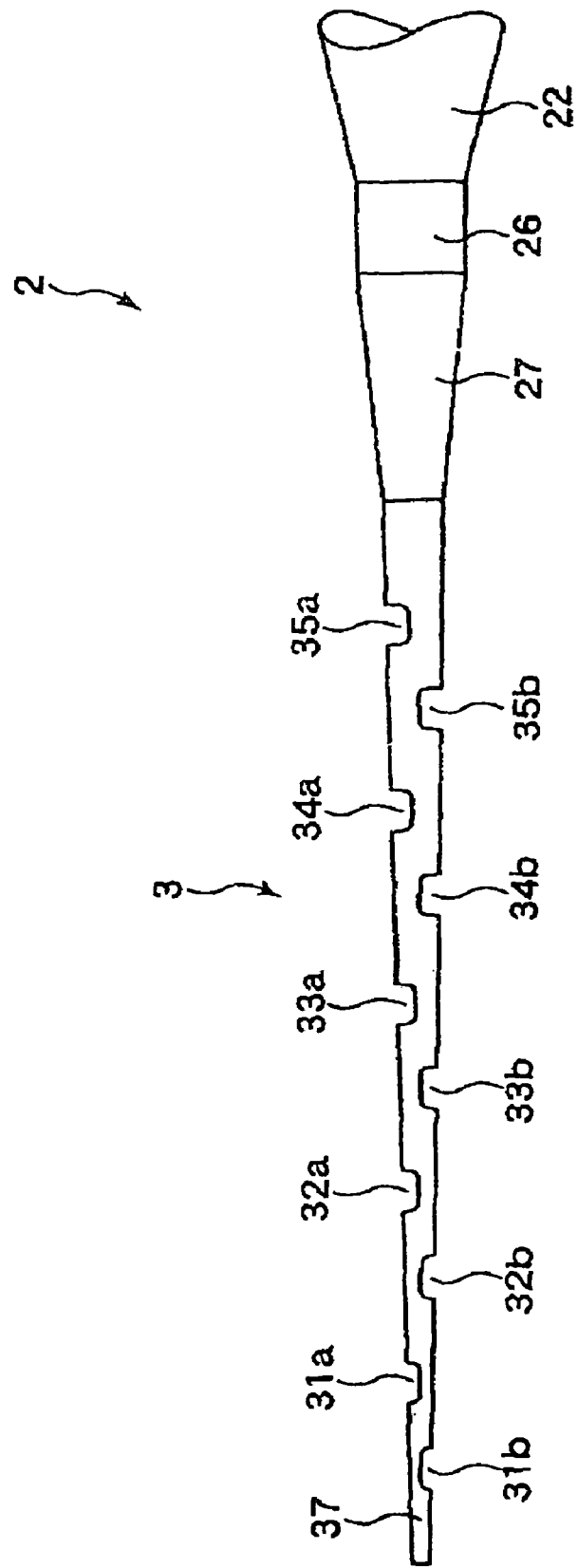
FIG. 6 is a side view of a reshapeable section according to a third embodiment of the guide wire.
Figure 7:
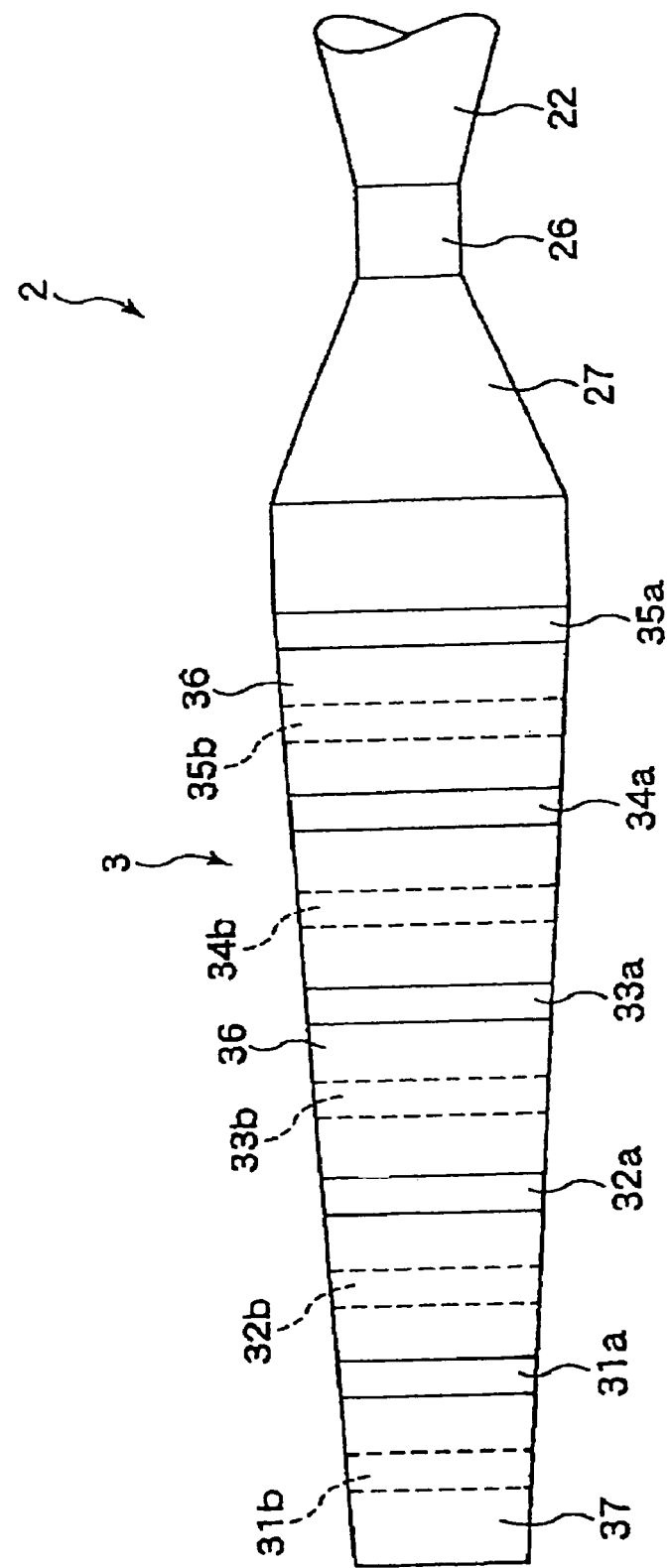
FIG. 7 is a plan view of the reshapeable section in the third embodiment of the guide wire.

FIGS. 6 and 7 illustrate a reshapeable section of a guide wire according to a third embodiment. The following description will primarily describe aspects of the third embodiment of the guide wire which differ from the first and second embodiments described above. Features in the third embodiment of the guide wire that are the same as or similar to those in the first and second embodiments are identified by the same reference numerals used in the embodiments described above, and a detailed description of such features is not repeated.

For convenience of description, the right side in FIGS. 6 and 7 is referred to as the proximal side or proximal end (proximal direction), the left side is referred to as the distal end or distal side (or distal direction), the upper side is referred to as the upper side (or upper direction) and the lower side is referred to as the lower side (or lower direction).

The present embodiment is the same as the second embodiment described above and shown in FIGS. 4 and 5, except that the configuration of the reshapeable section 3 is different.

As shown in FIGS. 6 and 7, the reshapeable section 3 is plate-shaped, and is provided in its upper surface and lower surface respectively with grooves 31a-35a and grooves 31b-35b which are the same as or similar to those in the second embodiment.

In the second embodiment above, the width and the thickness of the plate-shaped reshapeable section 3 are uniform in the longitudinal direction of the reshapeable section 3 and over the entire longitudinal extent of the reshapeable section 3. In this third embodiment, on the other hand, the reshapeable section 3 has a part where the width and the thickness of the plate-shaped reshapeable section 3 gradually decrease (continuously decrease) along the distal direction. Specifically, in the part on the distal side of the groove 35a (proximal-most groove 25a) of the reshapeable section 3, the width and the thickness of the reshapeable section 3 gradually decrease along the distal direction.

This configuration helps facilitate a more fine reshaping of the distal end portion of the reshapeable section 3, particularly as the distal end of the reshapeable section 3 is approached. In other words, the reshapeable section 3 can be reshaped into a more complicated or finer shape (for example, a more acutely curved or bent shape) on the distal side than on the proximal side.

While both the width and the thickness of the reshapeable section 3 decrease gradually along the distal direction in this embodiment, this configuration is not limitative. Specifically, the reshapeable section 3 may have a part where either one of, and only one of, the width and the thickness of decreases gradually along the distal direction.

In addition, while the width and the thickness of the reshapeable section 3 decrease continuously along the distal direction, the guide wire is not necessarily limited in this regard. Specifically, the reshapeable section 3 may have a part where the width and/or the thickness decreases in a stepwise manner along the distal direction.

The part where the width decreases along the distal direction and the part where the thickness decreases along the distal direction may not necessarily coincide with each other (i.e., they need not axially overlap with one another along the longitudinal direction), and both of them may partly overlap each other, or they may be positioned so that they do not overlap each other at all. Examples of such a situation include a configuration in which only the width decreases along the distal direction in a proximal part of the reshapeable section 3, only the thickness decreases along the distal direction in a distal part of the reshapeable section 3, and both the width and the thickness are decreased along the distal direction or are constant in an intermediate part of the reshapeable section.

Figure 8:
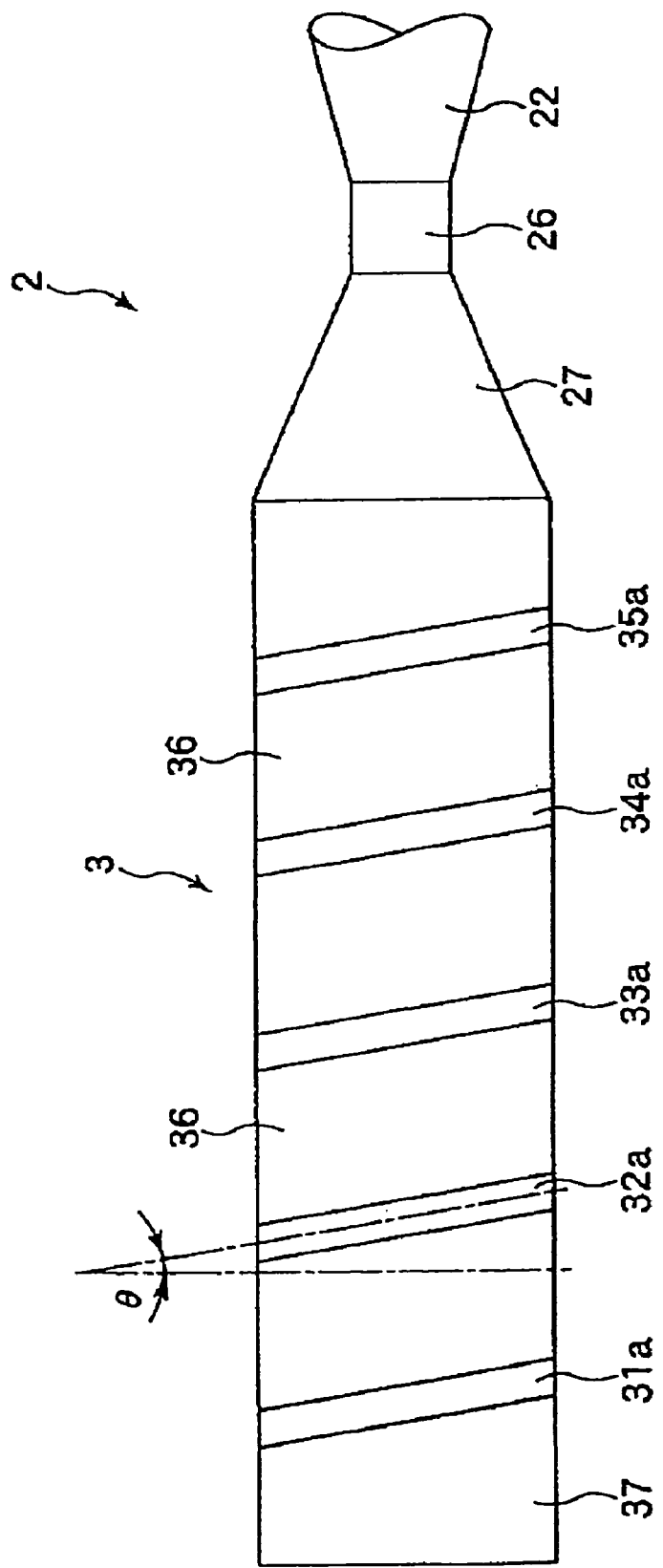
FIG. 8 is a plan view of a reshapeable section according to a fourth embodiment of the guide wire.

FIG. 8 illustrate a reshapeable section of a guide wire according to a fourth embodiment. The following description will primarily describe aspects of the fourth embodiment of the guide wire which differ from the embodiments described above. Features in the fourth embodiment of the guide wire that are the same as or similar to those in the earlier described embodiments are identified by the same reference numerals used in the embodiments described above, and a detailed description of such features is not repeated.

The fourth embodiment is the same as the first embodiment described above, except that the configuration of the reshapeable section 3 is different.

As shown in FIG. 8, the reshapeable section 3 is plate-shaped, and is provided in its upper surface (one side of the plate-shaped section) with grooves 31a-35a similar to those in the first embodiment. In the first embodiment, the grooves 31a-35a extend in a direction parallel to the width direction of the plate-shaped reshapeable section 3. In this fourth embodiment, on the other hand, the grooves 31a-35a each extend in a direction inclined at a predetermined angle (an angle other than zero degrees or 180°) to the width direction (the vertical direction in FIG. 8) of the reshapeable section 3.

The inclination angles θ of the grooves 31a-35a relative to the width direction may be the same or different. Examples of the latter case include a configuration in which the inclination angle θ increases (or decreases), continuously or stepwise, along the distal direction of the reshapeable section 3.

The inclination angle θ is not particularly limited. However, normally, it is preferably about 5 to 70°, more preferably about 10 to 30°.

In this embodiment, like in the second embodiment, both sides of the plate-like shape of the reshapeable section 3 may be provided respectively with the grooves 31a-35a and the grooves 31b-35b. In this case, it is preferable that both the grooves 31a-35a and the grooves 31b-35b are each inclined at an inclination angle θ relative to the width direction of the reshapeable section 3.

In addition, while the grooves 31a-35a do not intersect in the configuration shown in FIG. 8, this is not limitative. For example, the groove formation pattern may be one in which all or some of the grooves intersect or are branched.

Figure 9:
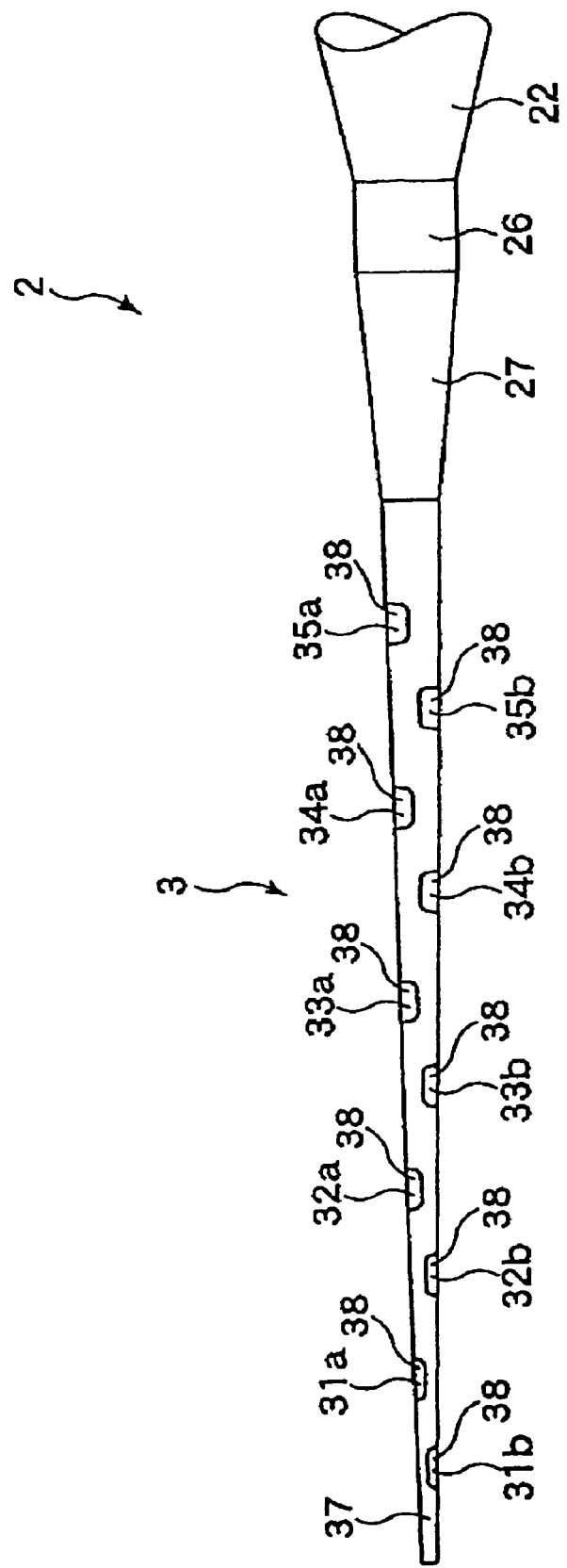
FIG. 9 is a side view of a reshapeable section according to a fifth embodiment of the guide wire.

FIG. 9 illustrate a reshapeable section of a guide wire according to a fifth embodiment. The following description will primarily describe aspects of the fifth embodiment of the guide wire which differ from the embodiments described above (primarily the first and third embodiments described above). Features in the fifth embodiment of the guide wire that are the same as or similar to those in the earlier described embodiments are identified by the same reference numerals used in the embodiments described above, and a detailed description of such features is not repeated.

The fifth embodiment is the same as the third embodiment described above, except that the configuration of the reshapeable section 3 is different.

As shown in FIG. 9, the reshapeable section 3 is plate-shaped, and has a part where the width and the thickness gradually decrease (continuously decrease) along the distal direction. This part is provided in its upper surface and lower surface respectively with grooves 31a-35a and grooves 31b-35b which are the same as or similar to those in the third embodiment.

The grooves 31a-35a and 31b-35b are filled with a malleable metal 38. The malleable metal 38 is supplied into the grooves and secured to the inside surfaces of the grooves by such a method as flame spraying, welding, plating, vapor deposition, sputtering, etc.

When a bending stress is exerted on one of the portions provided with the grooves 31a-35a and 31b-35b (groove formed portions) of the reshapeable section 3, the malleable metal 38 filling (secured to) the groove undergoes plastic deformation (spreading, compression or the like), resulting in that the groove formed portion as a whole is plastically deformed, and the shape upon the deformation is relatively securely maintained. In other words, with the grooves 31a-35a and 31b-35b filled with the malleable metal 38, shape retention after deformation can be enhanced.

In the present embodiment, a configuration in which the malleable metal is secured to the whole body of the reshapeable section 3 so as to render the whole part of the reshapeable section 3 susceptible to plastic deformation is not adopted. Instead, a configuration is adopted in which the malleable metal is secured partly to the reshapeable section (i.e., at spaced apart locations) so that only the groove formed portions are made to be susceptible to plastic deformation. With this arrangement, it is possible to overcome the drawback of other known guide wire constructions, namely the problem that the whole part of the reshapeable section 3 is hardened more than required, thereby lowering the flexibility or elasticity of the distal part of the guide wire 1.

Examples of the malleable metal 38 which can be used to fill the grooves include Au and Au alloys (for example, Au—Cu alloys containing 1 to 50 wt. % of Cu, Au—Ag alloys containing 1 to 50 wt. % of Ag, and Au—Pt alloys containing 1 to 50 wt. % of Pt). Here, Au and Au alloys (particularly, Au—X alloys containing 1 to 50 wt. % of X, where X is at least one selected from among Cu, Ag and Pt) are excellent in malleability and in adhesion to the inside surfaces of the grooves 31a to 35a and 31b to 35b, and also in chemical stability, and are therefore preferable.

The amounts (weights) of the malleable metal 38 loaded in the grooves 31a-35a and 31b-35b may be the same or different. For example, the loading amount (weight) of the malleable metal 38 may be gradually increased or decreased along the distal direction of the reshapeable section 3 (namely, sequentially in the order of the grooves 35a, 35b, 34a, 34b, 33a, 33b, 32a, 32b, 31a and 31b). In the former case (the amount is increased), the shape retention performance after deformation increases along the distal direction of the reshapeable section 3. In the latter case (the amount is decreased), the shape retention performance after deformation increases along the proximal direction of the reshapeable section 3.

In addition, the compositions of the malleable metals 38 filling the grooves 31a-35a and 31b-35b may be the same or different. For example, a configuration may be adopted in which Au (pure gold) is used as the malleable metal 38 for the grooves 31a, 31b, 32a, 32b located comparatively on the distal side of the reshapeable section 3, whereas an Au—X alloy or alloys containing 1 to 50 wt. % of X (for example, an Au—Cu alloy containing 1 to 50 wt. % of Cu) are used as the malleable metal(s) 38 for the other grooves 33a, 33b to 35a, 35b.

This embodiment of the guide wire involves each of the grooves 31a-35a and 31b-35b being filled with the malleable metal 38. However, this arrangement is not necessarily a requirement. For example, a configuration may be adopted in which the grooves 31a, 31b, 32a, 32b located comparatively on the distal side are filled with the malleable metal(s) 38, whereas the other grooves 33a, 34a, 35a, 33b, 34b, 35b are not filled with the malleable metal 38.

In addition, the configuration in which all or some of the grooves are filled with the malleable metal(s) 38 can also be applied, in the same manner, to all the other embodiments than the fifth embodiments.

FIG. 8 illustrate a reshapeable section of a guide wire according to a sixth embodiment. The following description will primarily describe aspects of the sixth embodiment of the guide wire which differ from the embodiments described above, primarily the first embodiment. Features in the sixth embodiment of the guide wire that are the same as or similar to those in the earlier described embodiments (e.g., the first embodiment) are identified by the same reference numerals used in the embodiments described above, and a detailed description of such features is not repeated.

The sixth embodiment is the same as the first embodiment described above, except that the configuration of the reshapeable section 3 is different.

Figure 10:
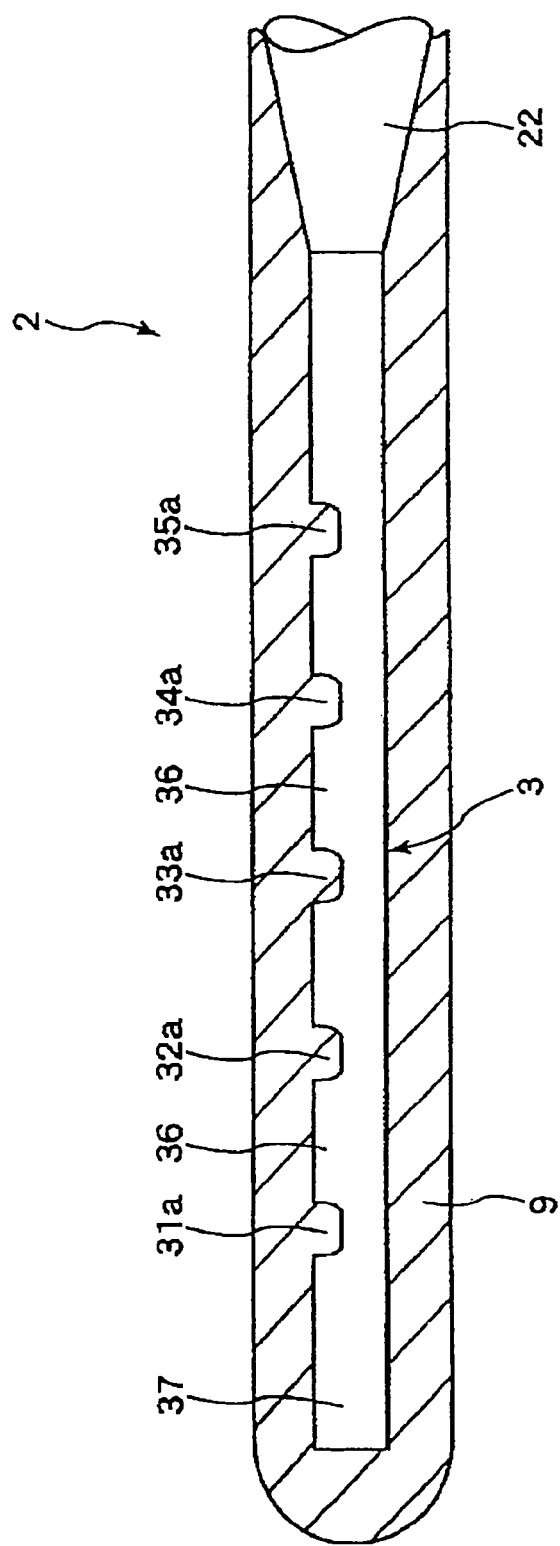
FIG. 10 is a side view of a reshapeable section according to a sixth embodiment of the guide wire.

As shown in FIG. 10, on the distal side of a first tapered section 22, a reshapeable section 3 is formed as one body with the first tapered section 22. The reshapeable section 3 is in the shape of a bar which is circular (inclusive of substantially circular) in cross section so as to be in the shape of a round bar. The bar-shaped reshapeable section 3 has an advantage over the above-described plate-shaped reshapeable section 3 in that it can be reshaped in a three-dimensional manner, i.e., it has a broad range of (a high degree of freedom in) selection of shape.

The outer peripheral surface (outer surface) of such bar-shaped reshapeable section 3 is provided with the grooves 31a-35a similar to those in the first embodiment at intervals along the longitudinal direction of the reshapeable section 3. In this case, in the reshapeable section 3, the grooves 31a-35a are formed partly in the outer peripheral portion of the reshapeable section 3 (upper part of FIG. 10), meaning that each of the grooves does not extend around the entire circumferential extent of the reshapeable section 3.

In the present embodiment, the characteristics such as the shapes, dimensions, intervals, etc. of the grooves 31a-35a are similar to those described in the first embodiment above, and, description of them is therefore omitted.

Figure 14:
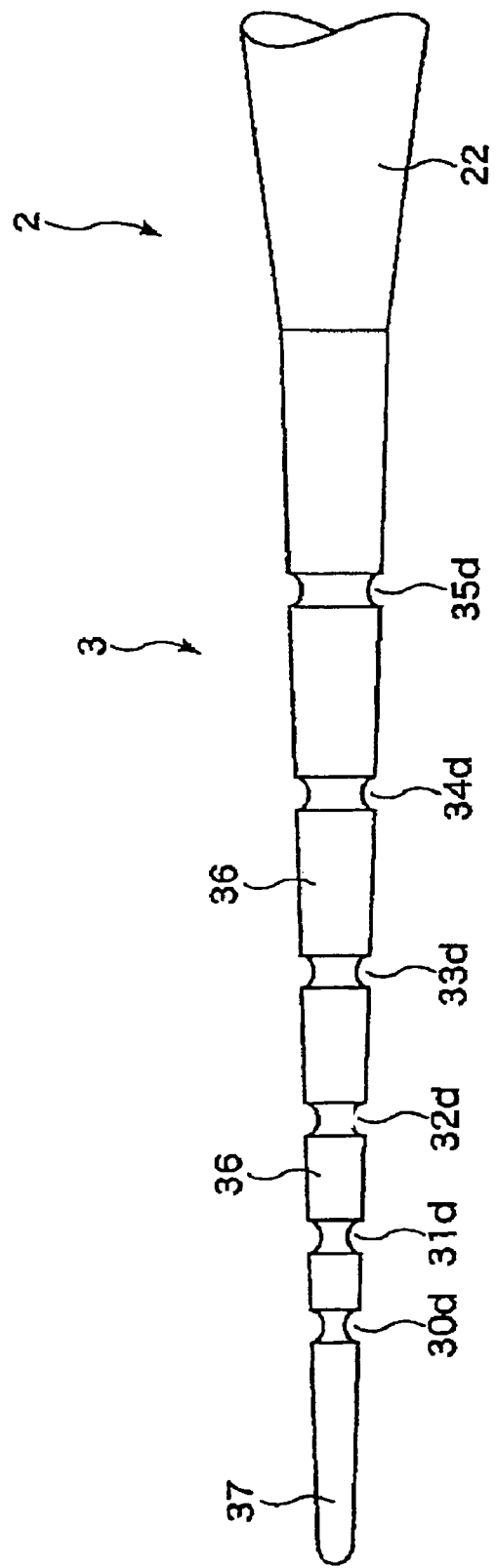
FIG. 14 is a side view of a reshapeable section according to a tenth embodiment of the guide wire.

While the outer diameter of the reshapeable section 3 is uniform along the longitudinal direction of the reshapeable section 3 in the present embodiment, this is not limitative. For example, the outer diameter of the reshapeable section 3 may be gradually decreased along the distal direction, i.e., the reshapeable section 3 may be tapered, as shown in FIG. 14.

In addition, the cross-sectional shape of the bar-shaped reshapeable section 3 is not limited to a circular cross-sectional shape. For example, the bar-shaped section can possess an elliptical cross-sectional shape or a polygonal cross-sectional shape such as a triangular cross-sectional shape, a tetragon cross-sectional shape (e.g., square, rhombus, trapezoid), a hexagonal cross-sectional shape, a octagonal cross-sectional shape, etc.

The outer periphery of the wire body 10 (first wire 2) is covered with a resin coating layer 9 similar to the above-mentioned resin coating layer 8 (a coil similar to the coil 5 in the first embodiment is not provided). Particularly, the outer periphery of the reshapeable section 3 is covered with the resin coating layer 9. The thickness of the resin coating layer 9 is greater on the outer periphery of the reshapeable section 3 than on that portion of the wire body 10 which is on the proximal side relative to the reshapeable section 3. In addition, the distal end (tip) of the resin coating layer 9 is preferably rounded in shape.

The resin coating layer 9 may be formed also for the purpose of enhancing safety in inserting the guide wire 1 into a blood vessel or the like. For this purpose, the resin coating material 9 is preferably made of a material rich in flexibility (soft material, elastic material).

Examples of the material rich in flexibility include polyolefins such as polyethylene, polypropylene, etc., polyvinyl chloride, polyesters (PET, PBT, etc.), polyamides, polyimides, polyurethane, polystyrene, silicone resins, thermoplastic elastomers such as polyurethane elastomers, polyester elastomers, polyamide elastomers, etc., various rubber materials such as latex rubbers, silicone rubbers, etc., and composite materials obtained by combining two or more of these. Among these materials, particularly preferred are polyurethane, silicone resins, thermoplastic elastomers, and silicone rubbers.

Since the reshapeable section 3 has the grooves 31a-35a, when the resin coating layer 9 is provided, part of the material constituting the layer enters into the inside of the grooves 31a-35a, thereby exhibiting an anchoring effect. Therefore, the adhesion of the resin coating layer 9 to the reshapeable section 3 is high, so that delamination of the resin coating layer 9 is prevented even upon reshaping the reshapeable section 3 into a desired shape.

It is to be understood that it is also possible to omit the resin coating layer 9.

Also, a coil similar to the above-mentioned coil 5 may be disposed around the outer periphery of the reshapeable section 3. Such a coil is preferably wound in the state of touching or being in secure contact with the reshapeable section 3. In addition, such a coil can be arranged for the purpose of imparting radiopaqueness to that portion of the guide wire 1 where the reshapeable section 3 is present.

Figure 11:
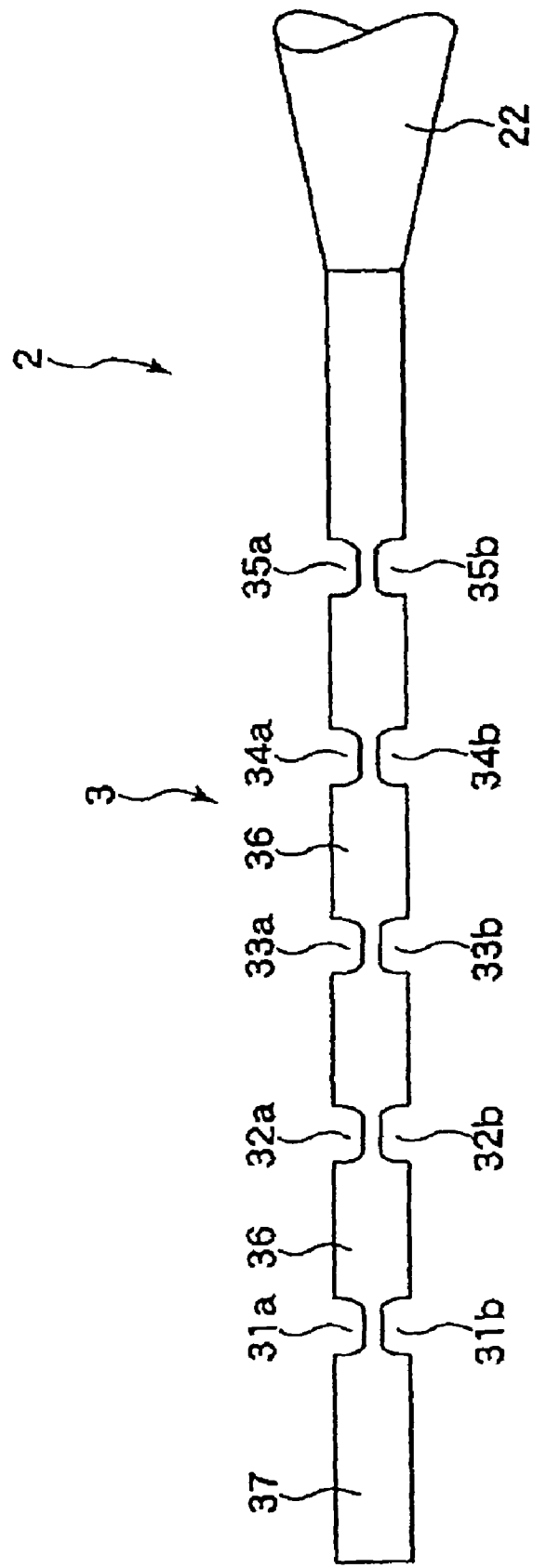
FIG. 11 is a side view of a reshapeable section according to a seventh embodiment of the guide wire according to the invention.

FIG. 11 illustrate a reshapeable section of a guide wire according to a seventh embodiment. The following description will primarily describe aspects of the seventh embodiment of the guide wire which differ from the embodiments described above, primarily the first and sixth embodiments. Features in the seventh embodiment of the guide wire that are the same as or similar to those in the earlier described embodiments (e.g., the first and sixth embodiments) are identified by the same reference numerals used in the embodiments described above, and a detailed description of such features is not repeated.

The seventh embodiment is the same as the sixth embodiment described above, except that the configuration of the reshapeable section 3 is different. Also, for convenience of description, the upper side in FIG. 11 is referred to as the upper side and the lower side is referred to as the lower side.

In this seventh embodiment, the reshapeable section 3 formed on the distal side of a first tapered section 22 is in the shape of a bar which is circular (inclusive of substantially circular) in cross section so as to be in the shape of a round bar, and is provided with a plurality of grooves in its outer peripheral surface. In this case, a surface on one side (upper surface) of the reshapeable section 3, and a surface on the other side (lower surface) of the reshapeable section 3 are provided. Thus, each of the grooves 31a-35a and 31b-35b does not extent around the entire circumferential extent of the bar-shaped reshapeable section 3 (i.e., each of the grooves extends around less than one-half of the circumferential extent of the bar-shaped reshapeable section 3). Also, the grooves 31*a*-35*a* on one side (one surface) of the reshapeable section 3 are positioned opposite respective ones of the grooves 31*b*-35*b* on the opposite side (opposite surface) of the reshapeable section 3, and the center axis of the reshapeable section 3 extends between the oppositely arranged pairs of grooves.

To be more specific, the upper surface of the reshapeable section 3 is provided with the grooves 31*a*-35*a* similar to those in the sixth embodiment at intervals along the longitudinal direction of the reshapeable section 3, and the lower surface of the reshapeable section 3 is provided with the grooves 31*b*-35*b* similar to the grooves 31*a*-35*a*. The grooves 31*a*-35*a* and the grooves 31*b*-35*b* are formed in the same shape at the same positions in the longitudinal direction of the reshapeable section 3.

The bar-shaped reshapeable section 3 is comparatively high in rigidity, as compared with the plate-like reshapeable section 3 mentioned above. However, since the reshapeable section 3 is provided with the grooves 31*a*-35*a* and the grooves 31*b*-35*b* respectively on the one-side surface (upper surface) and the other-side surface (lower surface) opposite to each other, with the center axis of the reshapeable section 3 therebetween, the reshapeable section 3 can be more easily reshaped into a desired shape.

In this embodiment, like the sixth embodiment of the guide wire described above, a resin coating layer 9 and a coil disposed around the outer periphery of the reshapeable section 3 may be provided in the same manner as described above.

Figure 12:
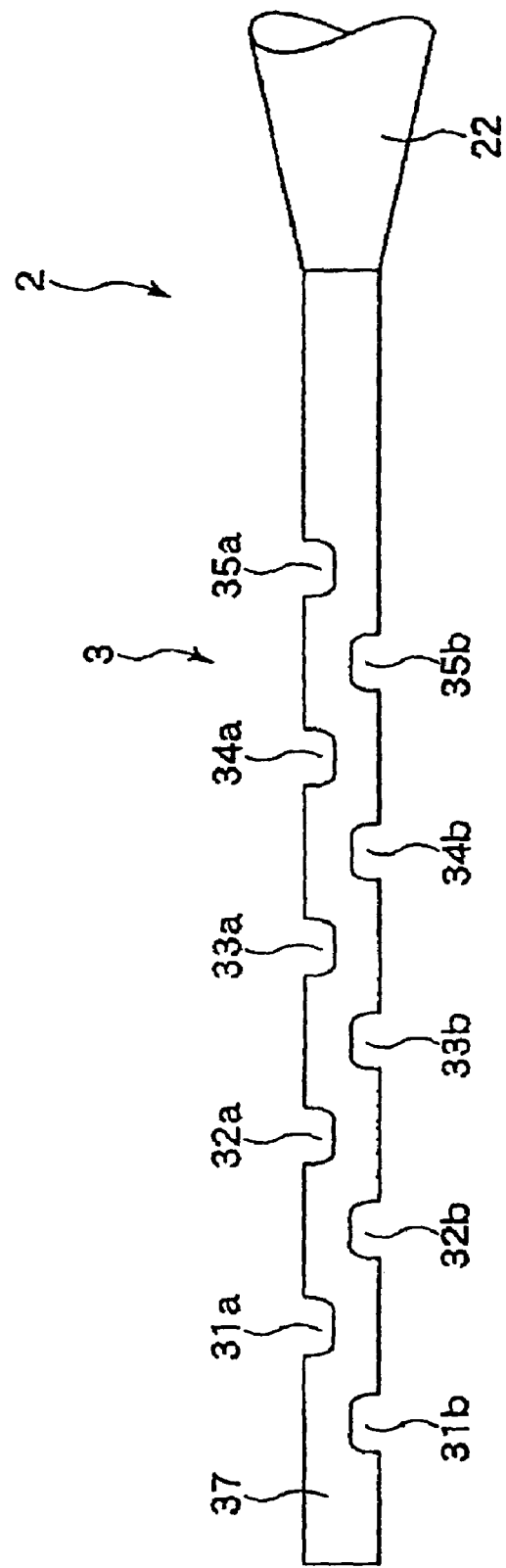
FIG. 12 is a side view of a reshapeable section according to an eighth embodiment of the guide wire.

FIG. 12 illustrate a reshapeable section of a guide wire according to an eighth embodiment. The following description will primarily describe aspects of the eighth embodiment of the guide wire which differ from the embodiments described above, primarily the first, second and sixth embodiments. Features in this eighth embodiment of the guide wire that are the same as or similar to those in the earlier described embodiments (e.g., the first, second and sixth embodiments) are identified by the same reference numerals used in the embodiments described above, and a detailed description of such features is not repeated.

For convenience of description, the upper side in FIG. 12 is referred to as the upper side and the lower side is referred to as the lower side.

The present embodiment is the same as the sixth embodiment, except the configuration of the reshapeable section 3. The reshapeable section 3 formed on the distal side of a first tapered section 22 is in the shape of a bar which is circular (inclusive of substantially circular) in cross section so as to be in the shape of a round bar, and is provided with a plurality of grooves in its outer peripheral surface. In this embodiment, grooves are provided on a surface on one side (upper surface) of the reshapeable section 3, and a surface of the reshapeable section 3 on the other side (lower surface), whereby the surfaces provided with the grooves are opposite to each other. Here, the grooves on one side are staggered relative to the grooves on the opposite side, with the center axis of the reshapeable section 3 extending between the two sets of grooves 31*a*-35*a* and 31*b*-35*b*.

To be more specific, the upper surface of the reshapeable section 3 is provided with the grooves 31*a*-35*a* similar to those in the sixth embodiment at intervals along the longitudinal direction of the reshapeable section 3, and the lower surface of the reshapeable section 3 is provided with the grooves 31*b*-35*b* like the grooves 31*a*-35*a*, at positions in an alternating relationship with the positions of the grooves 31*a*-35*a*, that is a stagger of half their pitch therebetween. In other words, the reshapeable section 3 in the eighth embodiment is the same as the reshapeable section 3 in the second embodiment, except that the reshapeable section 3 in this eight embodiment is bar-shaped.

Also, like all the preceding embodiments employing the bar-shaped reshapeable section 3, each of the grooves 31*a*-35*a* and 31*b*-35*b* does not extent around the entire circumferential extent of the bar-shaped reshapeable section 3 (i.e., each of the grooves extends around less than one-half of the circumferential extent of the bar-shaped reshapeable section 3).

The bar-like reshapeable section 3 is comparatively high in rigidity, as compared with the plate-like reshapeable section 3 mentioned above. However, since the one-side surface (upper surface) and the other-side surface (lower surface) opposite to each other, with the center axis of the reshapeable section 3 therebetween, are provided respectively with the grooves 31*a*-35*a* and the grooves 31*b*-35*b* in different patterns, any part in the longitudinal direction of the reshapeable section 3 can be curved (deformed) relatively freely toward the upper side and toward the lower side and into a fine shape, so that the reshapeable section 3 can wholly or partly be reshaped more finely.

In this embodiment also, a resin coating layer 9 and a coil disposed around the outer periphery of the reshapeable section 3 can also be provided in a manner as described above with the sixth embodiment.

Figure 13:
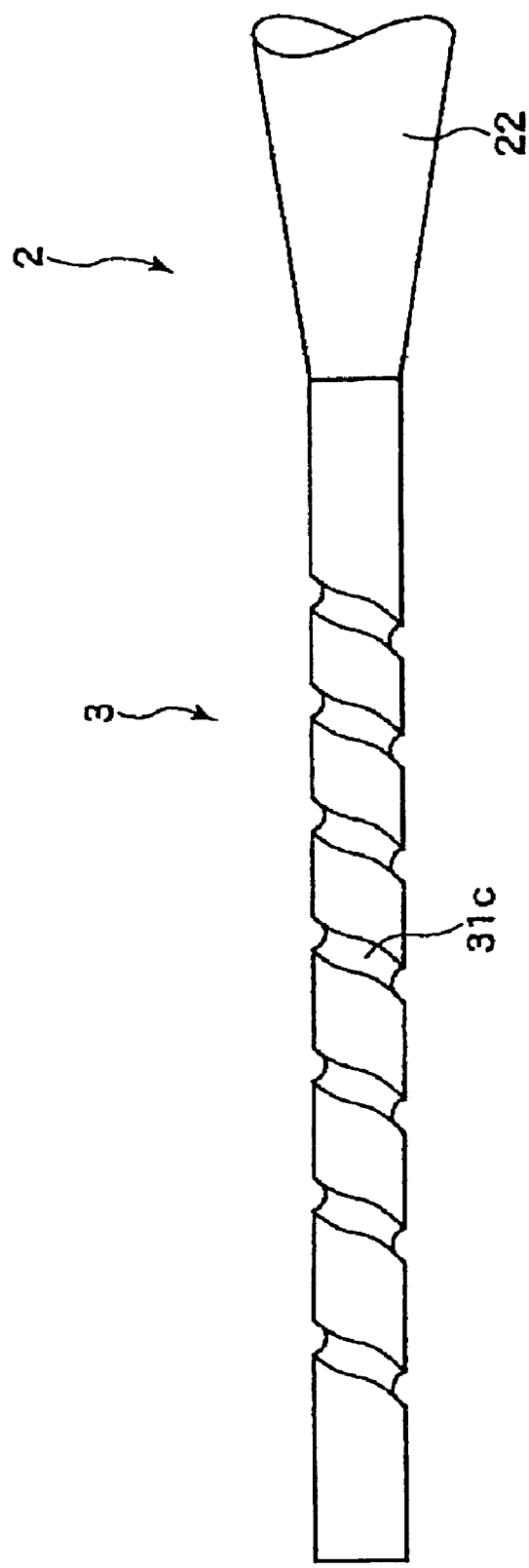
FIG. 13 is a side view of a reshapeable section according to a ninth embodiment of the guide wire.

FIG. 13 illustrate a reshapeable section of a guide wire according to a ninth embodiment. The following description will primarily describe aspects of the ninth embodiment of the guide wire which differ from the embodiments described above, primarily the first and sixth embodiments. Features in this ninth embodiment of the guide wire that are the same as or similar to those in the earlier described embodiments (e.g., the first and sixth embodiments) are identified by the same reference numerals used in the embodiments described above, and a detailed description of such features is not repeated.

The present embodiment is the same as the sixth embodiment, except for the configuration of the reshapeable section 3. The reshapeable section 3 formed on the distal side of a first tapered section 22 is in the shape of a bar which is circular (inclusive of substantially circular) in cross section so as to be in the shape of a round rod, and is provided in its outer peripheral surface with one or a plurality of spiral groove(s) 31*c*. With such a spiral groove(s) 31*c* provided, a distal part of the guide wire 1 can advantageously be rendered flexible.

The pitch of the groove 31*c* (the interval between the adjacent groove portions as measured along the longitudinal direction of the reshapeable section 3) may be uniform or varied along the longitudinal extent of the reshapeable section 3. Examples of the latter case (a varying pitch) include a configuration in which the pitch of the groove 31*c* decreases gradually in the distal direction of the reshapeable section 3. In this case, the density of the groove portions formed in the reshapeable section 3 is higher on the distal side than on the proximal side, so that the reshapeable section 3 can be reshaped into a more complicated or finer shape (for example, a more acutely curved or bent shape) on the distal side than on the proximal side.

In this embodiment also, a resin coating layer 9 and a coil disposed around the outer periphery of the reshapeable section 3 as described above in connection with the sixth embodiment can be applied.

FIG. 14 illustrate a reshapeable section of a guide wire according to a tenth embodiment. The following description will primarily describe aspects of the tenth embodiment of the guide wire which differ from the embodiments described above, primarily the first and sixth embodiments. Features in this tenth embodiment of the guide wire that are the same as or similar to those in the earlier described embodiments (e.g., the first and sixth embodiments) are identified by the same reference numerals used in the embodiments described above, and a detailed description of such features is not repeated.

This tenth embodiment is the same as the sixth embodiment, except the configuration of the reshapeable section 3 differs. The reshapeable section 3 formed on the distal side of a first tapered section 22 is in the shape of a bar having a circular (inclusive of substantially circular) cross section so as to be in the shape of a round rod. In this embodiment, the outer diameter of the reshapeable section 3 gradually decreases in the distal direction so that the reshapeable section 3 is tapered. This helps ensure that the reshapeable section 3 is gradually decreased in rigidity along the distal direction.

The reshapeable section 3 as just-mentioned is provided in its outer peripheral surface with a plurality of annular (ring-shaped) grooves at spaced intervals along the longitudinal direction of the reshapeable section 3. Specifically, the reshapeable section 3 is provided with the grooves 30$d$, 31$d$, 32$d$, 33$d$, 34$d$, 35$d$ arranged in this order from the distal side. Each of these grooves 30$d$-35$d$ extend around the entire circumferential extent of the reshapeable section 3.

In addition, with respect to the grooves 30$d$-35$d$, the groove pitch (the interval between the adjacent grooves) gradually decreases along the distal direction. This helps ensures that the density of the grooves formed in the reshapeable section 3 is higher on the distal side than on the proximal side. This, together with the above-mentioned fact that the outer diameter of the reshapeable section 3 gradually decreases in the distal direction, results in the reshapeable section 3 possessing the ability to be reshaped into a more complicated or finer shape (for example, a more acutely curved or bent shape) on the distal side than on the proximal side.

While the outer diameter of the reshapeable section 3 is gradually varied along the longitudinal direction of the reshapeable section 3, this is not limitative. By way of example, a configuration may be adopted in which the reshapeable section 3 has a part where the outer diameter is varied stepwise (particularly, decreased stepwise along the longitudinal direction).

In this embodiment, the outer diameter of the reshapeable section 3 may be uniform along the longitudinal direction, and the pitch of the grooves 30$d$-35$d$ may be constant along the longitudinal direction of the reshapeable section 3.

In the present embodiment also, a resin coating layer 9 described in the sixth embodiment and a coil disposed around the outer periphery of the reshapeable section 3 also described in connection with the sixth embodiment, can be provided.

The configuration in which the density of the grooves in the reshapeable section 3 is varied along the longitudinal direction of the reshapeable section 3, particularly the configuration in which the reshapeable section 3 has a part where the density of the grooves increases in the distal direction, is applicable to all of the first to tenth embodiments described above.

In addition, the number, shapes, positions, etc. of the grooves in the reshapeable section are not limited to those in the embodiment shown in the drawings. The grooves can also be formed in patterns such as a lattice-like pattern and a net-like pattern.

It is to be understood that two or more of the configurations of the guide wires according to the first to tenth embodiments described above and shown in the drawing figures may be combined.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. For example, parts or features of the guide wire can be replaced by other features or parts exhibiting the same or similar functional characteristics. In addition, features beyond those described here can be used in the guide wire. Accordingly, it is expressly intended that all such variations, changes and equivalents which fall within the spirit and scope of the present invention as defined in the claims, be embraced thereby.

What is claimed is:

1. A guide wire comprising:
a wire body comprised of a plurality of sections including an elongate reshapeable section, an elongate constant diameter section and an elongate tapering section;
the constant diameter section having an outer diameter that is constant along an entirety of a longitudinal extent of the constant diameter section;
the tapering section having an outer diameter that tapers from a larger outer diameter to a smaller outer diameter toward the reshapeable section;
the constant outer diameter section and the tapering section both being positioned proximally of the reshapeable section;
the elongate reshapeable section being made of a super-elastic alloy and possessing an outer circumferential surface;
a plurality of spaced apart grooves formed in the outer circumferential surface of the reshapeable section, each groove extending around less than half the outer circumferential surface of the reshapeable section, and each groove extending in a direction different from the longitudinal direction of the reshapeable section; and
wherein the reshapeable section is plate-shaped having oppositely positioned sides, the grooves being provided in both sides of the plate-shaped reshapeable section.

2. A guide wire comprising:
a wire body comprised of a proximal part and a distal part, the distal part being located distally of the proximal part;
an elongate reshapeable section provided at the distal part of the wire body, the elongate reshapeable section extending in a longitudinal direction and possessing an outer surface;
the outer surface of the reshapeable section being provided with a plurality of grooves extending in a direction different from the longitudinal direction of the reshapeable section; and
wherein the reshapeable section is plate-shaped having oppositely positioned sides, the grooves being provided in at least one of the sides of the plate-shaped reshapeable section.

3. The guide wire as set forth in claim 2, wherein the reshapeable section is plate-shaped having oppositely positioned sides, the grooves being provided on both of the oppositely positioned sides of the plate-shaped reshapeable section.

4. The guide wire as set forth in claim 3, wherein the grooves on one of the sides of the reshapeable section are positioned in staggered relation, along the longitudinal direction of the reshapeable section, to the grooves on the opposite side of the reshapeable section.

5. A guide wire comprising:
a wire body comprised of a proximal part and a distal part, the distal part being located distally of the proximal part;
an elongate reshapeable section provided at the distal part of the wire body, the elongate reshapeable section extending in a longitudinal direction and possessing an outer surface;
the outer surface of the reshapeable section being provided with at least two grooves extending in a direction different from the longitudinal direction of the reshapeable section; and
wherein the reshapeable section is plate-shaped having oppositely positioned sides, the at least one groove being provided in at least one of the sides of the plate-shaped reshapeable section.

* * * * *